(12) United States Patent
Melnick et al.

(10) Patent No.: US 8,338,464 B2
(45) Date of Patent: Dec. 25, 2012

(54) SMALL MOLECULE INHIBITORS OF BCL6

(75) Inventors: Ari Matthew Melnick, New York, NY (US); Alexander D. MacKerell, Jr., Baltimore, MD (US); Gilbert Gerard Privé, Toronto (CA)

(73) Assignees: Albert Einstein College of Medicine of Yeshiva University, Bronx, NY (US); University Health Network, Toronto (CA); University of Maryland, Baltimore, Baltimore, MD (US)

( * ) Notice: Subject to any disclaimer, the term of this patent is extended or adjusted under 35 U.S.C. 154(b) by 252 days.

(21) Appl. No.: 12/312,800

(22) PCT Filed: Nov. 29, 2007

(86) PCT No.: PCT/US2007/024571
§ 371 (c)(1),
(2), (4) Date: Jan. 20, 2010

(87) PCT Pub. No.: WO2008/066887
PCT Pub. Date: Jun. 5, 2008

(65) Prior Publication Data
US 2010/0130564 A1    May 27, 2010

Related U.S. Application Data

(60) Provisional application No. 60/872,466, filed on Nov. 30, 2006.

(51) Int. Cl.
*A61K 31/426* (2006.01)
(52) U.S. Cl. ............ 514/365; 514/367; 514/360
(58) Field of Classification Search ........... 514/357, 514/360, 369
See application file for complete search history.

(56) References Cited

U.S. PATENT DOCUMENTS 6,525,072 B1  2/2003  Tang et al.
2004/0214872 A1 * 10/2004  Suto et al. ............... 514/369

FOREIGN PATENT DOCUMENTS

WO    WO 98/07835 A2    2/1998

OTHER PUBLICATIONS

Johnson et al.; Relationships between drug activity and NCI preclinical in vitro and in vivo models and early clinical trials; British Journal of Cancer; (2001) 84 (10), 1424-1431.*
Voskoglou-Nomikos et al.; Clinical Predictive Value of the in Vitro Cell Line, Human Xenograft, and Mouse Allograft Preclinical Cancer Models; Clinical Cancer Research; vol. 9: 4227-4239; Sep. 15, 2003.*
Bos et al.; Protein expression of B-cell lymphoma gene 6 (BCL-6) in invasive breast cancer is associated with cyclin D1 and hypoxia-inducible factor 1__ (HIF-1__); Oncogene (2003); vol. 22, pp: 8948-8951.*
PCT International Search Report for PCT Application No. PCT/US2007/024571.
Written Opinion for PCT Application No. PCT/US2007/024571.
Deininger, M W N et al, entitled "BCR-ABL Tyrosine Kinase Activity Regulates the Expression of Multiple Genes Implicated in the Pathogenesis of Chronic Myeloid Leukemia," Cancer Research, 60, 2049-2055, Apr. 1, 2000, http://cancerres.aacrjournals.org/cgi/content/full/60/7/2049, 19 pages.
PCT International Search Report for PCT Application No. PCT/US2007/024571, Aug. 7, 2008.
Written Opinion for PCT Application No. PCT/US2007/024571, Aug. 7, 2008.

* cited by examiner

*Primary Examiner* — Michele K Joike
*Assistant Examiner* — Antonio Galisteo Gonzalez
(74) *Attorney, Agent, or Firm* — Amser, Rothstein & Ebenstein

(57) ABSTRACT

Provided are methods of inhibiting BCL6 repression in a mammalian cell. Also provided are methods of treating cancer in a mammal.

12 Claims, 11 Drawing Sheets

Compound 1

Compound 2

5272683

5261485

5568198

5320052

5321906

Compound 3

K509-0005

3136-0205

3660-0343

0896-2057

4577-0580

4191-0382

Compound 3

Compounds 4 and 5

COMPOUND 4
5558536

COMPOUND 5
3448-8474

COMPOUND 5
5808641 -

SMALL MOLECULE INHIBITORS OF BCL6

This is a U.S. national phase of PCT Application No. PCT/US2007/024571, filed Nov. 29, 2007, which claims the benefit of U.S. Provisional Application No. 60/872,466, filed Nov. 30, 2006.

BACKGROUND OF THE INVENTION (1) Field of the Invention

The present invention generally relates to inhibitors of protein action. More specifically, the invention is directed to the identification of small molecule inhibitors of BCL6.

(2) Description of the Related Art

The BTB domain (also known as the POZ domain) is a common protein-protein interaction motif that is found in over 180 human proteins (Stogios et al., 2005). The domain has been found in proteins that are implicated in many biological processes, including central nervous system development, oocyte maturation, eye development, hematopoiesis, apoptosis, immunity, and protein degradation. BTB domain proteins are widely represented in eukaryotic genomes, and are roughly as abundant as SH3 domain proteins. One major class of BTB proteins consists of a single N-terminal BTB domain, a middle linker region, and a set of C-terminal $C_2H_2$ zinc-finger domains, and at least 43 such BTB-ZF genes have been identified in the human genome (Srogios et al., 2005). These proteins are also known as the POK proteins (Maeda et al., 2005). Many BTB-ZF proteins have been implicated in cancer, including BCL6 (Albagli-Curiel, 2003; Polo et al., 2004; Cattoretti et al., 2005), PLZF (Costoya and Pandolfi, 2001; McConnell et al., 2003), LRF/Pokemon (Maeda et al., 2005), HIC1 (Chen et al., 2004; Pinte et al., 2004), Miz-1 (Peulert et al., 1997; Phan et al., 2005), and Kaiso (Prokhortchouk et al., 2006). In general, the zinc fingers from these proteins are responsible for binding to specific regulatory sites on the DNA, while the BTB domain is a protein-protein interaction module that dimerizes and functions to modulate the transcriptional activity of the factors.

Both the BCL6 and PLZF proteins consist of an N-terminal BTB domain, followed by a central region of several hundred residues that are predicted to have little or no fixed 3D structure, and end with a series of $C_2H_2$-type zinc finger domains at the C-terminus. This general type of architecture is seen in 43 of the over 200 known human BIB domain proteins (GGP and P. J. Stogios, xtal.uhnres.utoronto.ca/prive/btb.html). A second major class of BTB domain proteins contain C-terminal ketch β-propeller repeats, and many of these are thought to be involved in cytoskeletal functions, although some of these are involved in transcription regulation (Adams et al., 2000). The core BTB domain fold is also found in the T1 domain of voltage-gated channels (Kreusch et al., 1998), and in the ElonginC/Skp1 proteins (Stebbins et al., 1999).

Despite the architectural similarity of the BTB/zinc finger transcription factors, these can function as repressors, activators, or both and the BIB domain plays a central role in these activities (Kaplan and Calame, 1997; Kobayashi et al., 2000; Mahmoudi et al., 2002). The majority of BTB/zinc finger proteins, however, are thought to be transcriptional repressors, and several of these mediate their effects through the recruitment of histone deacetylase complexes. Thus, in BCL6, the BIB domain mediates interactions with the SMRT, N-CoR, BCoR and mSin3A corepressors, as well as with histone deacetylase 1 (HDAC-1), and repression is relieved with HDAC inhibitors (David et al., 1998; Dhordain et al., 1997; Dhordain et al., 1998; Grignani et al., 1998; Guidez et al., 1998; He et al., 1998; Hong et al., 1997; Huynh and Bardwell, 1998; Huynh et al., 2000; Lin et al., 1998; Wong and Privalsky, 1998). The recruitment of a histone deacetylase complex is not a universal property of the BTB domain, as evidenced by the fact that the BTB domains of HIC1 and gFBP-B do not interact with these factors (Deltour et al., 1999). Thus, it is clear that distinct mechanisms are used by different BTB domains in order to carry out a variety of biological effects.

In the B-cell lineage, the BCL6 protein is expressed in germinal center (GC) B-cells, but not in pre-B cells or in differentiated progenies such as plasma cells. Because BCL6 expression is tightly regulated during lymphoid differentiation, its down-regulation in post-GC B-cells may be necessary for further plasma/memory cell differentiation. Some of the more notable genes that are repressed by BCL6 include the B lymphocyte-induced maturation protein (blimp-1), a transcriptional repressor of c-myc which plays a key role in differentiation of B-cells to plasma cells (Shaffer et al., 2002), the cell cycle control genes p27kip1 and cyclin D2 (Shaffer et al., 2000), the programmed cell death-2 protein (PDCD2) (Baron et al., 2002), and B7-1/CD80 (Niu et al., 2003). Chromosomal translocations upstream of the BCL6 gene are observed in approximately 30-40% of diffuse large B-cell lymphomas (DLBCL) and in 5-14% of follicular lymphomas (FL) (Kuppers and Dalla-Favera, 2001; Niu, 2002; Ye, 2000). In addition, the promoter region of BCL6 is targeted by somatic hypennutation in GC B-cells (Pasqualucci et al., 2003; Shen et al., 1998; Wang et al., 2002). Thus, a B-cell with an activated BCL6 gene may be trapped at the GC stage due to the repression of differentiation and cell-cycle control proteins (Calame et al., 2003; Dent et al., 2002; Fearon et al., 2001; Staudt, 2002). In addition to its role in lymphoid cells, BCL6 represses the expression of the chemokines MCP-1, MCP3 and MRP-1 in macrophages and is an important negative regulator of TH-2 type inflammation (Toney et al., 2000).

The BCL6 site of corepressor binding has been identified, and peptides having the sequence of the corepressor binding site inhibit corepressor binding to BCL6. That inhibition causes apoptosis of B-cell lymphoma cells expressing BCL6. See WO 2005/058939 A2. In that work, a recombinant BCL6 peptide inhibitor (BPI) was designed based on the BCL6/SMRT crystal. BPI could disrupt the formation of the BCL6/SMRT complex on target gene promoters, reactivate BCL6 target gene expression in lymphoma cells and could phenocopy the BCL6 null phenotype in vivo (i.e. loss of germinal center formation in response to T-cell dependent antigens) (Polo et al., 2004). As alluded to above, BPI has potent anti-lymphoma activity, and killed BCL6 positive DLBCL and BL cell lines in vitro and in vivo (in xenotransplants) but had no effect on BCL6 negative lymphoma cell lines (Polo et al., 2004). Moreover, there was no toxicity observed in animals injected daily even with up to 1.5 mg of BPI per day (Polo et al., 2004; unpublished data). Those results indicate that BCL6 is an excellent therapeutic target and that lateral groove blockade is a potent and specific strategy for abrogating its activity in lymphoma cells.

Based on the above, it is apparent that small molecule inhibitors of BCL6 would be useful for cancer treatments. The present invention describes such BCL6 inhibitors.

SUMMARY OF THE INVENTION

Accordingly, the inventors have identified compounds that inhibit BCL6 repression. Thus, the invention is directed to methods of inhibiting BCL6 repression in a mammalian cell, the method comprising contacting the BCL6 with Compound 1, Compound 2, Compound 3, Compound 4, or Compound 5, wherein
Compound 1 is

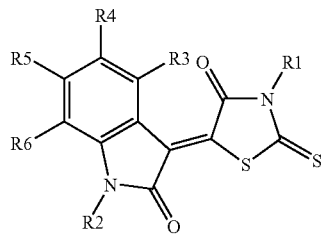

wherein R1 is H, a hydroxy, a halogen, a formyl, an acyl, a carboxy, a keto, an amido, a carbamoyl, a guanidino, a ureido, an amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, and R2-R6 are independently H, a hydroxy, a halogen, a formyl, an acyl, a carboxy, a keto, an amido, a carbamoyl, a guanidino, a ureido, an amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R2-R6, or any combination thereof;

Compound 2 is

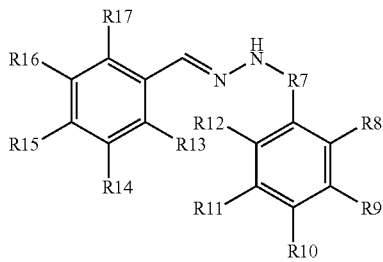

wherein R7 is

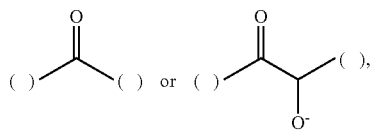

and R8-R17 are independently H, a hydroxy, a halogen, a formyl, an acyl, a carboxy, a keto, an amido, a carbamoyl, a guanidino, a ureido, an amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, provided that R14 and R15 are not both hydroxy;

Compound 3 is

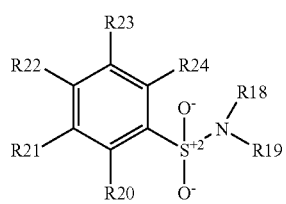

wherein R18 and R19 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing R18 and R19, or any combination thereof, provided neither R18 nor R19 comprises more than one amido; and R20-R24 are independently H, a hydroxy, a halogen, a formyl, an acyl, a keto, an amido, a carbamoyl, a guanidino, a ureido, a amidino, a thiol, a thioether, a mercapto, a sulfinyl, a sulfonyl, a sulfonamide, a cyanide, an amidine, a carbamate, an amide, an imine, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, an aromatic ring encompassing any two adjacent members of R20-R24, or any combination thereof;

Compound 4 is

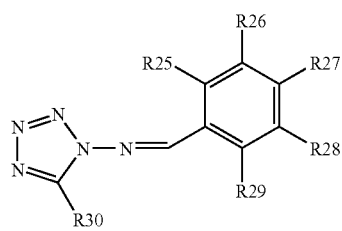

wherein R25-R29 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R25-R29, or any combination thereof; and Compound 5 is

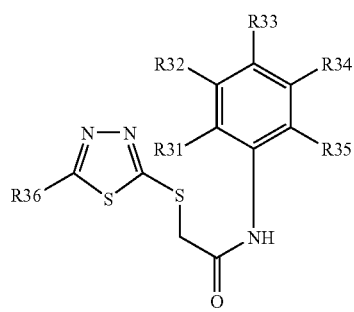

wherein R31-R35 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_2$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, and R36 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group.

The invention is also directed to methods of treating cancer in a mammal, the method comprising administering to the mammal an amount of Compound 1, Compound 2, Compound 3, Compound 4, or Compound 5 to the mammal effective to treat cancer in the mammal, wherein Compound 1 is

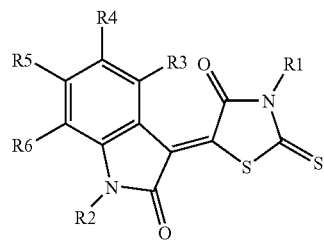

wherein R1 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, and R2-R6 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R2-R6, or any combination thereof;

Compound 2 is

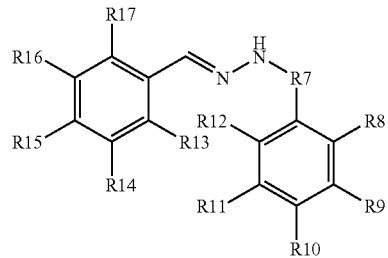

wherein R7 is

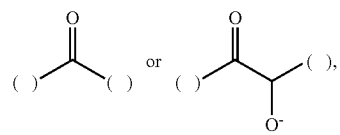

and R8-R17 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an inline, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, provided that R14 and R15 are not both hydroxy;

Compound 3 is

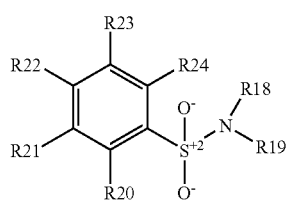

wherein R18 and R19 are independently H, a hydroxy, a halogen, a formyl, an acyl, a carboxy, a keto an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing R18 and R19, or any combination thereof, and R20-R24 are independently H, a hydroxy, a halogen, a formyl, an acyl, a carboxy, a keto, an amido, a carbamoyl, a guanidino, a ureido, a amidino, a thiol, a thioether, a mercapto, a sulfinyl, a sulfonyl, a sulfonamide, a cyanide, an amidine, a carbamate, an amide, an imine, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, an aromatic ring encompassing any two adjacent members of R20-R24, or any combination thereof;

Compound 4 is

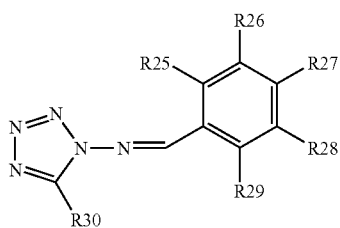

wherein R25-R29 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R25-R29, or any combination thereof; and Compound 5 is

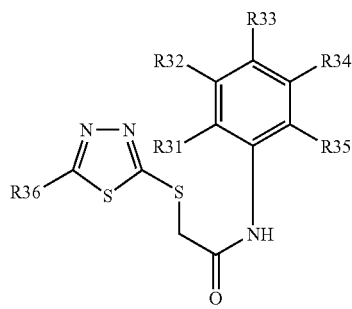

wherein R31-R35 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an inline, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_2$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, and R36 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group.

DETAILED DESCRIPTION OF THE INVENTION

Figure 1:
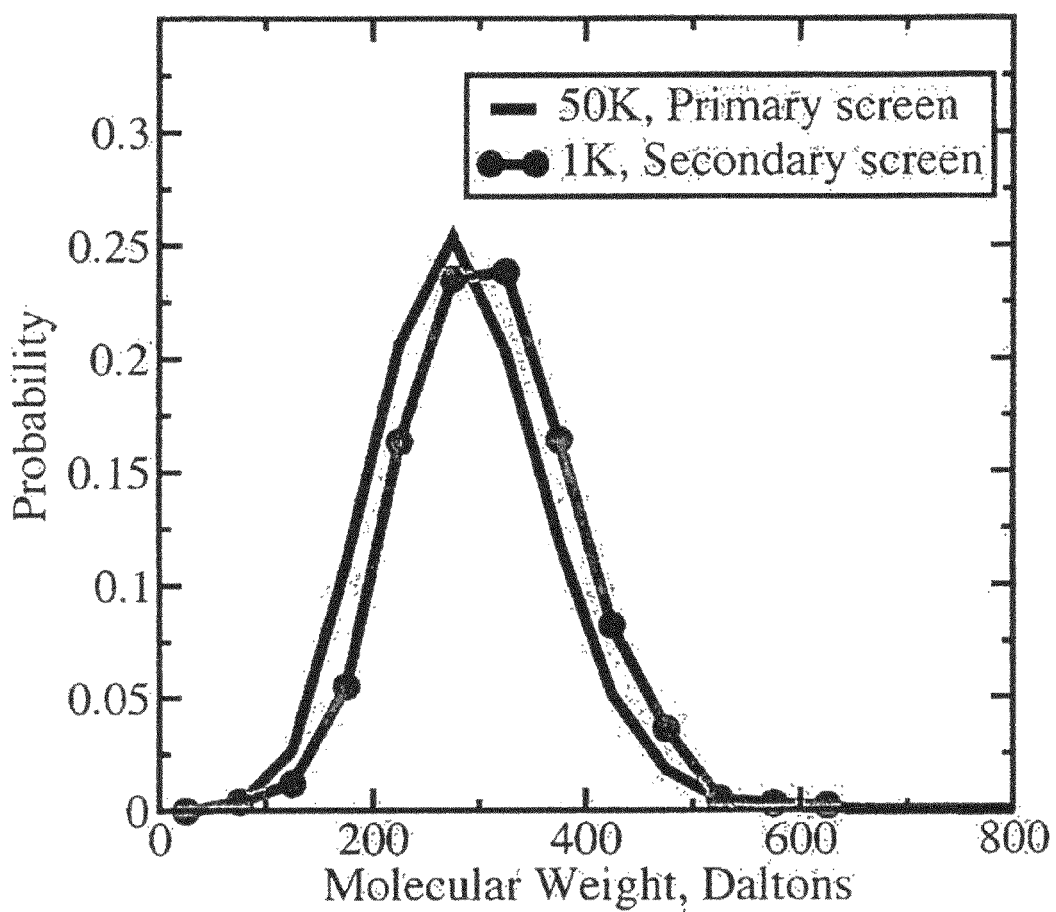
FIG. 1 is a graph of the molecular weight distribution of compounds selected from the primary and secondary screens. The majority of compounds have MWs of ~300 Dal., an ideal range for compounds to be optimized.

The present invention is based on the identification of several classes of compounds that inhibit BCL6 repression. See Example. Without being bound by any particular mechanism, it is believed that the BCL6 inhibition by these compounds is due to the compounds' binding to the BCL6 corepressor binding site.

Thus, the invention is directed to methods of inhibiting BCL6 repression in a mammalian cell. The methods comprise contacting the BCL6 with Compound 1, Compound 2, Compound 3, Compound 4, or Compound 5, wherein
Compound 1 is

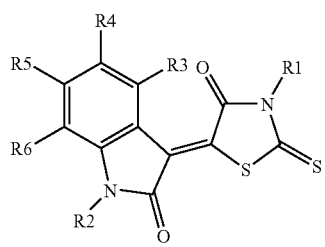

wherein R1 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, and R2-R6 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R2-R6, or any combination thereof;

Compound 2 is

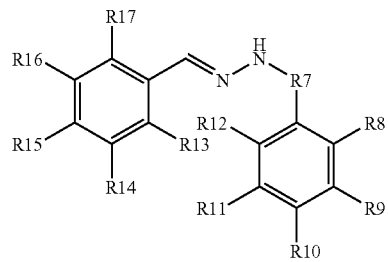

wherein R7 is

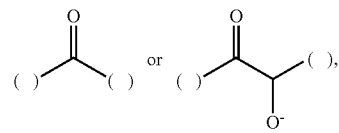

and R8-R17 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, provided that R14 and R15 are not both hydroxy;

Compound 3 is

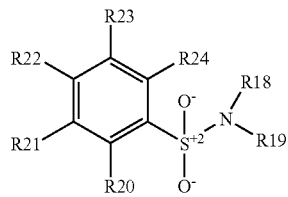

wherein R18 and R19 are independently H, a hydroxy, a halogen, a formyl, an acyl, a carboxy, a keto, an amido, a carbamoyl, a guanidino, a ureido, a amidino, an amino, a thiol, a thioether, a mercapto, a sulfinyl, a sulfonyl, a sulfonamide, a cyanide, an amidine, a carbamate, an inline, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing R18 and R19, or any combination thereof, provided neither R18 nor R19 comprises more than one amido; and R20-R24 are independently H, a hydroxy, a halogen, a formyl, an acyl, a keto, an amido, a carbamoyl, a guanidino, a ureido, a amidino, a thiol, a thioether, a mercapto, a sulfinyl, a sulfonyl, a sulfonamide, a cyanide, an amidine, a carbamate, an amide, an imine, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, an aromatic ring encompassing any two adjacent members of R20-R24, or any combination thereof;

Compound 4 is

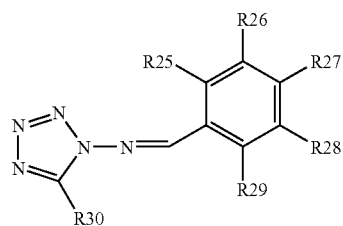

wherein R25-R29 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R25-R29, or any combination thereof; and Compound 5 is

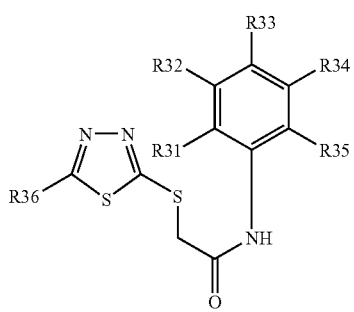

wherein R31-R35 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_2$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, and R36 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrite, or heterocyclic group.

As used herein, the terms "halo" or "halogen" refer to Cl, Br, F or I substituents.

As used herein, when referring to alternative substituents of moieties, the term "combination thereof" includes the use of one substituent as a substitution for another substituent, for example, "a halogen, an aryloxy, or any combination thereof" includes a halogen as a substitution for an H on the aryloxy moiety.

As used herein, an amine includes primary, secondary and tertiary amines.

Preferably in these methods,

R1 comprises a carboxy;

R2 is H or a carboxy, a $C_1$-$C_3$ alkyl or alkenyl, or any combination thereof;

R3-R6 are independently H or a halogen;

R8-R12 are independently H or a halogen;

R13-R17 are independently H, a hydroxy, or a halogen;

R18 and R19 are independently H, a halogen, a $C_1$-$C_3$ alkyl, alkenyl, ketone, secondary amine or heterocyclic group, an amide, a nitro, a thioether, an acetyl, an aryl, a heteroaryl, a fused aryl, a fused heteroaryl, or any combination thereof, wherein R18 can alternatively be a sulfinate condensed with R24;

R20-R23 are independently H, or a halogen;

R24 is H, a halogen or a sulfinate condensed with R18;

R25-R29 are independently H, a halogen or a hydroxy;

R30 is an amino; and/or

R31-R35 is independently H, a cyanide, a $C_1$-$C_3$ straight or branched alkyl or alkynyl or any combination thereof, provided that R34 and R35 are not both methyl.

More preferably,

R1 is

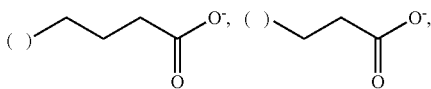

-continued

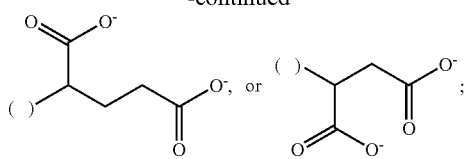

R2 is H, CH₃,

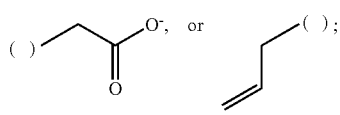

R3, R5 and R6 is H;
R4 is H or Br;
R8, R11 and R12 are H;
R9 and R10 are H or Br, wherein R9 and R10 are not both Br;
R13 is O⁻ or Br;
R14 is O⁻ or H;
R15 is H or Br;
R16 is H or O⁻;
R17 is 11;
one of R18 or R19 is H, CH₃, a sulfinate condensed with R24, or

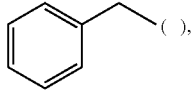

and the other of R18 or R19 is

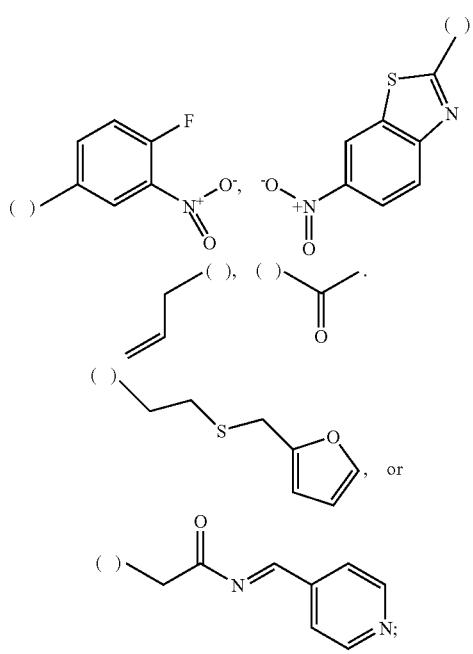

R20 and R21 is H;
R22 is H, Br or Cl;

R23 is H, R24 is H or a sulfinate condensed with one of R18 or R19, or R23 and R24 encompasses

where the two carbons are at R23 and R24;
R25-R29 are independently H, Cl or O⁻;
R30 is NH₂;
R31-R35 are H or

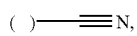

wherein one and only one R31-R35 is

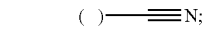

and/or
R36 is NH₂.

Thus, the invention method can comprise contacting the BCL6 with a Compound 1. Preferably, the Compound 1 is

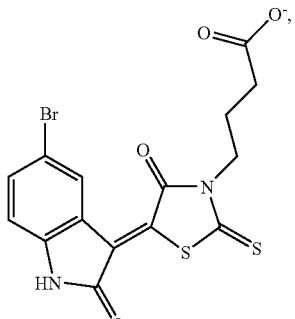

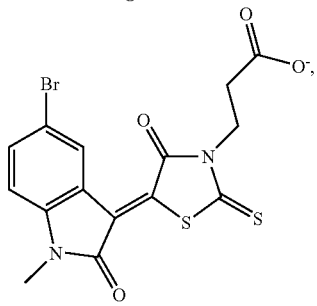

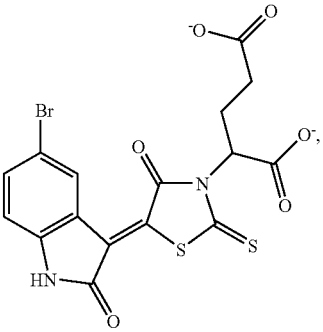

Figure 7:
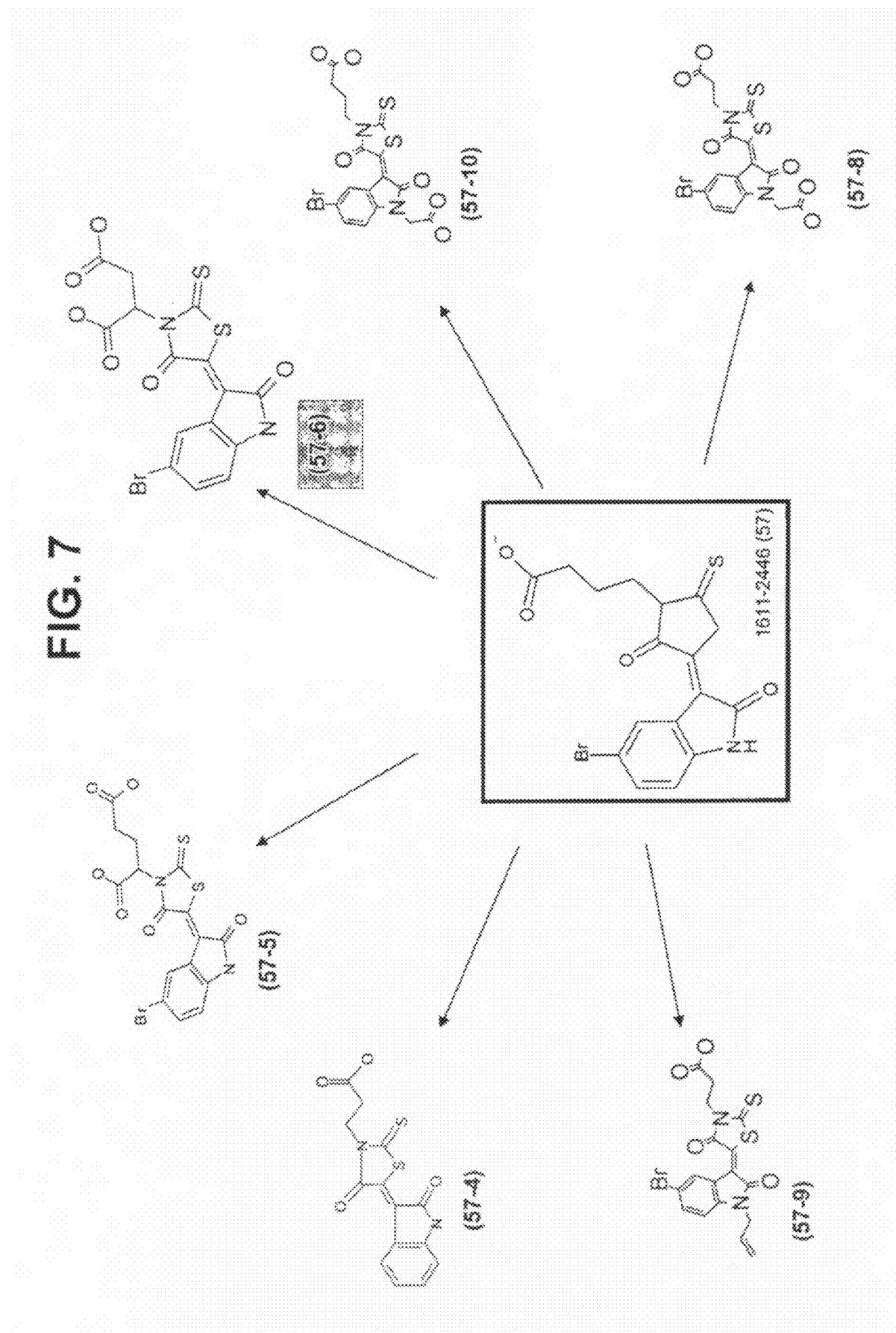
FIG. 7 depicts compounds from the 57 family, including compound 57-6.

-continued
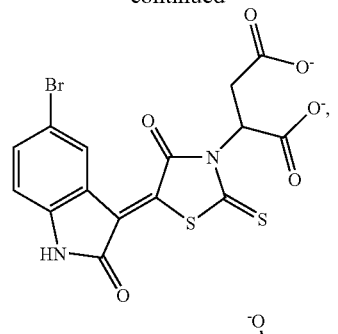
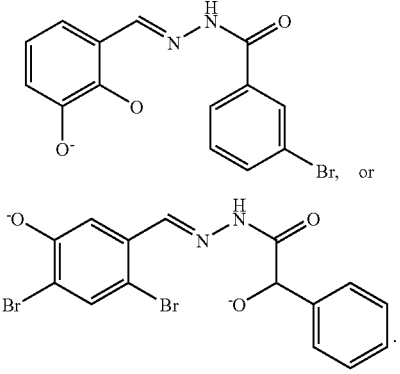
More preferably, Compound 1 is one of the compounds set forth in FIG. 7, and most preferably is compound 57-6.
The invention method can alternatively comprise contacting the BCL6 with a Compound 2. Preferably, the Compound 2 is
The invention method can alternatively comprise contacting the BCL6 with a Compound 3. Preferably, the Compound 3 is
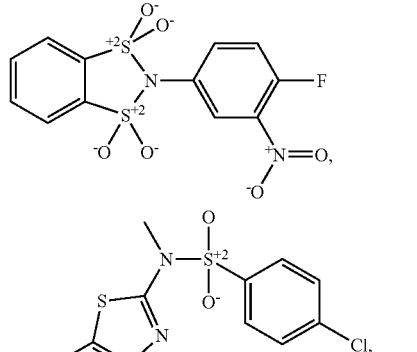
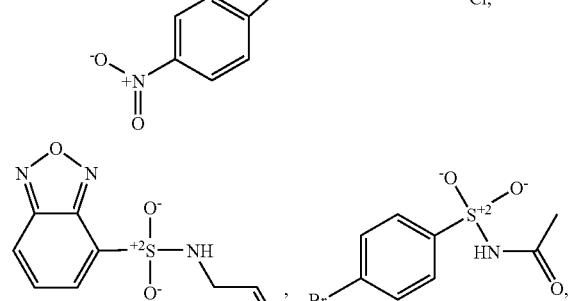
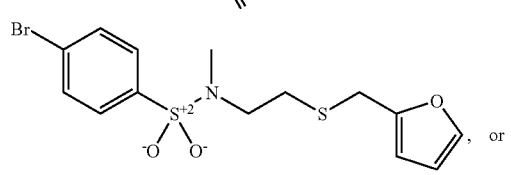
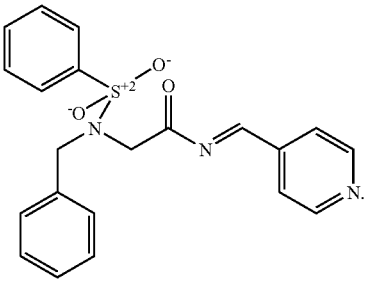

The method can alternatively comprise contacting the BCL6 with a Compound 4. Preferably, the Compound 4 is

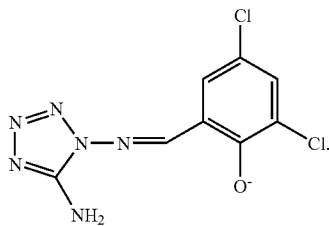

The method can alternatively comprise contacting the BCL6 with a Compound 5. Preferably, the Compound 5 is

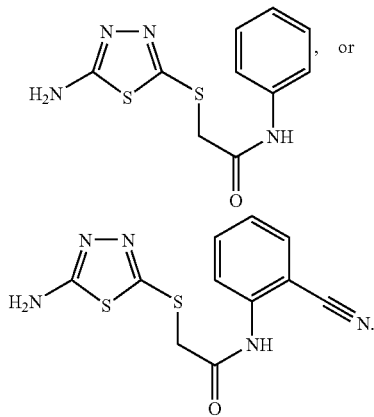

These methods are not narrowly limited to any particular mammalian cell. Preferably, the cell is a cancer cell, more preferably a lymphoma cell or a breast cancer cell.

The invention methods can be utilized on cells in vitro or, preferably, cells that are part of a mammal. Although these methods can be used in cells in any mammalian species, most preferably the mammal is a human.

When cells in mammals (e.g., humans) are treated with the invention inhibitors, it is preferred that the cells are treated by administering the inhibitor to the mammal, where the inhibitor is in a pharmaceutically acceptable carrier.

The above-described compounds can be formulated without undue experimentation for administration to a mammal, including humans, as appropriate for the particular application. Additionally, proper dosages of the compositions can be determined without undue experimentation using standard dose-response protocols.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added.

The parenteral preparation can be enclosed in ampules, disposable syringes or multiple dose vials made of glass or plastic.

The compositions designed for oral, nasal, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The compounds used in the methods of the invention may be administered per se (neat) or in the form of a pharmaceutically acceptable salt. When used in medicine, the salts should be both pharmacologically and pharmaceutically acceptable, but non-pharmaceutically acceptable salts may conveniently be used to prepare the free active compound or pharmaceutically acceptable salts thereof. Pharmacologically and pharmaceutically acceptable salts include, but are not limited to, those prepared from the following acids: hydrochloric, hydrobromic, sulphuric, nitric, phosphoric, maleic, acetic, salicyclic, p-toluenesulfonic, tartaric, citric, methanesulphonic, formic, malonic, succinic, naphthalene-2-sulphonic, and benzenesulphonic. Also, pharmaceutically acceptable salts can be prepared as alkaline metal or alkaline earth salts, such as sodium, potassium or calcium salts of the carboxylic acid group.

The compounds useful in the invention may be delivered in the form of anti-cancer cocktails. An anti-cancer cocktail is a mixture of any one of the imidazoles useful with this invention with another anti-cancer drug and/or supplementary potentiating agent. The use of cocktails in the treatment of cancer is routine. In this embodiment, a common administration vehicle (e.g., pill, table, implant, injectable solution, etc.) would contain both the imidazole useful in this invention and the anti-cancer drug and/or supplementary potentiating agent.

Anti-cancer drugs are well known and include: Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (V16-213); Floxuridine; Fluorouracil (5-FU); Flutamide; Hydroxyurea (hydroxycarbamide); Ifosfamide; Interferon Alfa-2a, Alfa 2b; Leuprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o. p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bis-guanylhydrazone; MGBG); Pentostatin; Semustine (methyl-CCNU); Teniposide (VM-26) and Vindesine sulfate.

Supplementary potentiating agents likewise are well characterized and include: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); Ca++ antagonists (e.g., verapamil, nifedipine, nitrendipine and caroverine); Calmodulin inhibitors (e.g., prenylamine, trifluoroperazine and clomipramine); Amphotericin (e.g., Tween 80 and perhexyline maleate); Triparanol analogues (e.g., tamoxifen); antiarrhythmic drugs (e.g., quinidine); antihypertensive drugs (e.g., reserpine); and Thiol depleters (e.g., buthionine and sulfoximine).

The invention is also directed to methods of treating cancer in a mammal. The methods comprise administering to the mammal an amount of Compound 1, Compound 2, Compound 3, Compound 4, or Compound 5 to the mammal effective to treat cancer in the mammal, wherein Compound 1 is

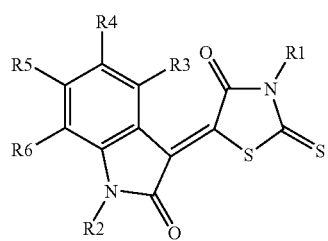

wherein R1 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, and R2-R6 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R2-R6, or any combination thereof;

Compound 2 is

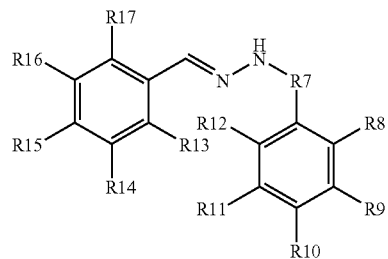

wherein R7 is

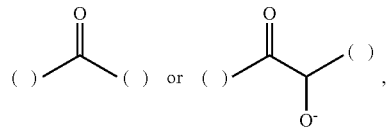

and R8-R17 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, provided that R14 and R15 are not both hydroxy;

Compound 3 is

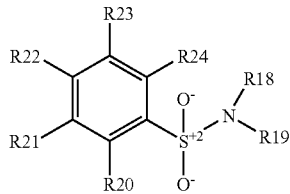

wherein R18 and R19 are independently H, a hydroxy, a halogen, a formyl, an acyl, a carboxy, a keto an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing R18 and R19, or any combination thereof, and R20-R24 are independently H, a hydroxy, a halogen, a formyl, an acyl, a carboxy, a keto, an amido, a carbamoyl, a guanidino, a ureido, a amidino, a thiol, a thioether, a mercapto, a sulfinyl, a sulfonyl, a sulfonamide, a cyanide, an amidine, a carbamate, an amide, an imine, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, an aromatic ring encompassing any two adjacent members of R20-R24, or any combination thereof;

Compound 4 is

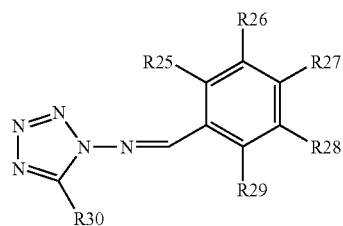

wherein R25-R29 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R25-R29, or any combination thereof; and Compound 5 is

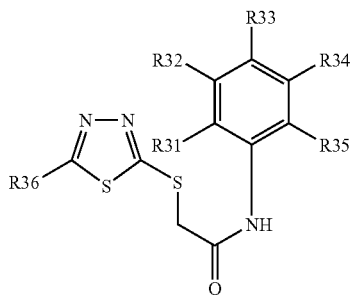

wherein R31-R35 are independently H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_2$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group, a ring encompassing any two adjacent members of R8-R17, or any combination thereof, and R36 is H, a hydroxy, a halogen, a formyl, an acyl, a carboxy, a keto, an amido, a carbamoyl, a guanidino, a ureido, a amidino, a nitro, an amino, a thiol, a thioether, a mercapto, a sulfinyl, a sulfonyl, a sulfonamide, a cyanide, an amidine, a carbamate, an imine, an amide, a hydrazine, an acetyl, an aminal, an alkoxy, an aryloxy, an aldehyde, an anhydride, an aryl, a heteroaryl, a carboxyaryl, a fused cycloalkyl, a fused heterocyclic group, a fused aryl, a fused heteroaryl, or a $C_1$-$C_{10}$ straight or branched alkyl, carboxyalkyl, cycloalkyl, alkenyl, carboxyalkenyl, cycloalkenyl, ketone, alkynyl, carboxyalkyl, cycloalkyl, ether, cycloether, amine, nitrile, or heterocyclic group.

Preferably,

R1 comprises a carboxy;

R2 is H or a carboxy, a $C_1$-$C_3$ alkyl or alkenyl, or any combination thereof;

R3-R6 are independently H or a halogen;

R8-R12 are independently H or a halogen;

R13-R17 are independently H, a hydroxy, or a halogen;

R18 and R19 are independently H, a halogen, a $C_1$-$C_3$ alkyl, alkenyl, ketone, secondary amine or heterocyclic group, an amide, a nitro, a thioether, an acetyl, an aryl, a heteroaryl, a fused aryl, a fused heteroaryl, or any combination thereof, wherein R18 can alternatively be a sulfinate condensed with R24;

R20-R23 are independently H, or a halogen;

R24 is H, a halogen or a sulfinate condensed with R18;

R25-R29 are independently H, a halogen or a hydroxy;

R30 is an amino; and/or

R31-R35 is independently H, a cyanide, a $C_1$-$C_3$ straight or branched alkyl or alkynyl or any combination thereof, provided that R34 and R35 are not both methyl.

More preferably,

R1 is

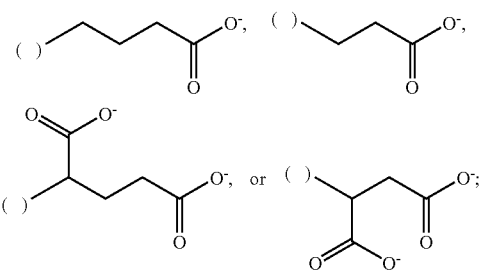

R2 is H, 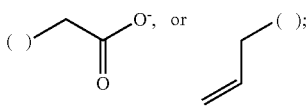

R3, R5 and R6 is H;
R4 is H or Br;
R8, R11 and R12 are H;
R9 and R10 are H or Br, wherein R9 and R10 are not both Br;
R13 is O⁻ or Br;
R14 is O⁻ or H;
R15 is H or Br;
R16 is H or O⁻;
R17 is H;
one of R18 or R19 is H, CH₃, a sulfinate condensed with R24, or

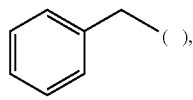

and the other of R18 or R19 is

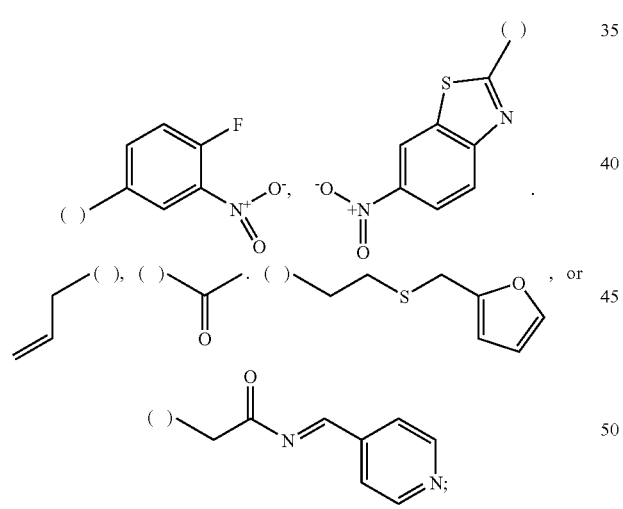

R20 and R21 is H;
R22 is H, Br or Cl;
R23 is H, R24 is H or a sulfinate condensed with one of R18 or R19, or R23 and R24 encompasses

where the two carbons are at R23 and R24;

R25-R29 are independently H, Cl or O⁻;
R30 is NH₂;
R31-R35 are H or

wherein one and only one R31-R35 is

and/or
R36 is NH₂.

Most preferably, the Compound 1, Compound 2, Compound 3, Compound 4, or Compound 5 is

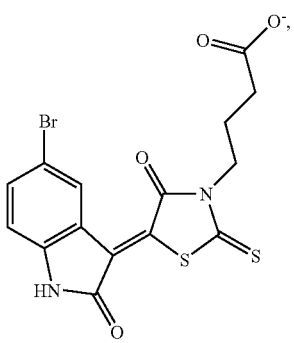

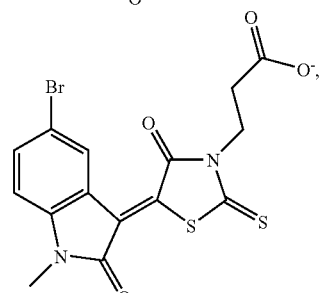

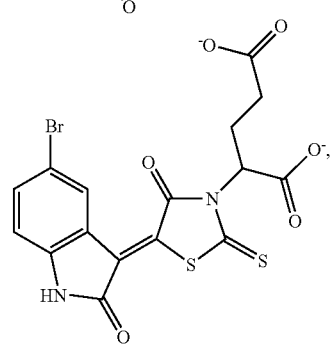

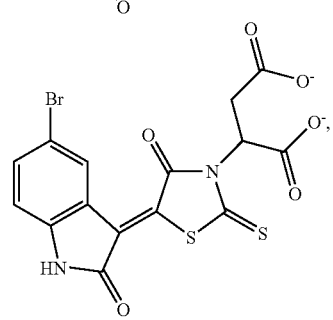

25
-continued
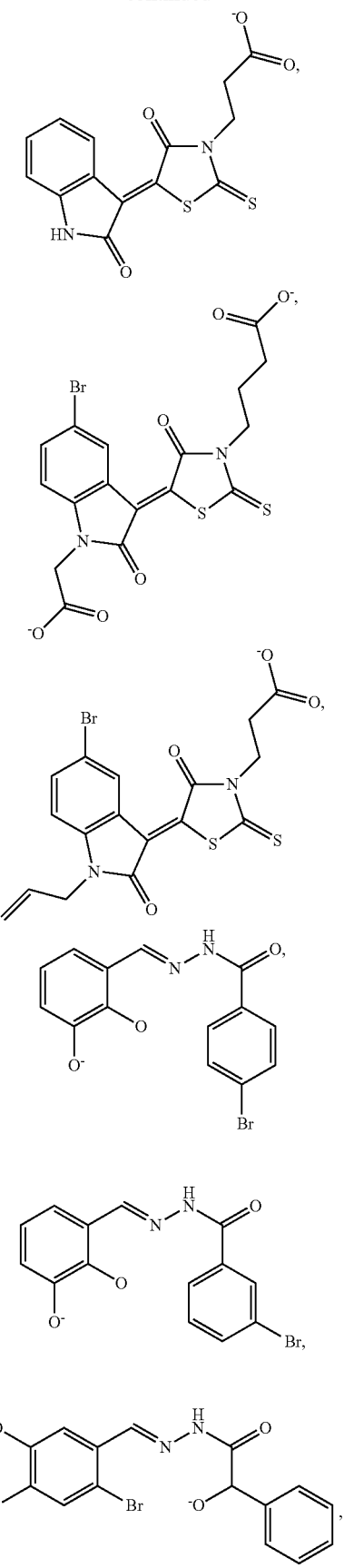
26
-continued
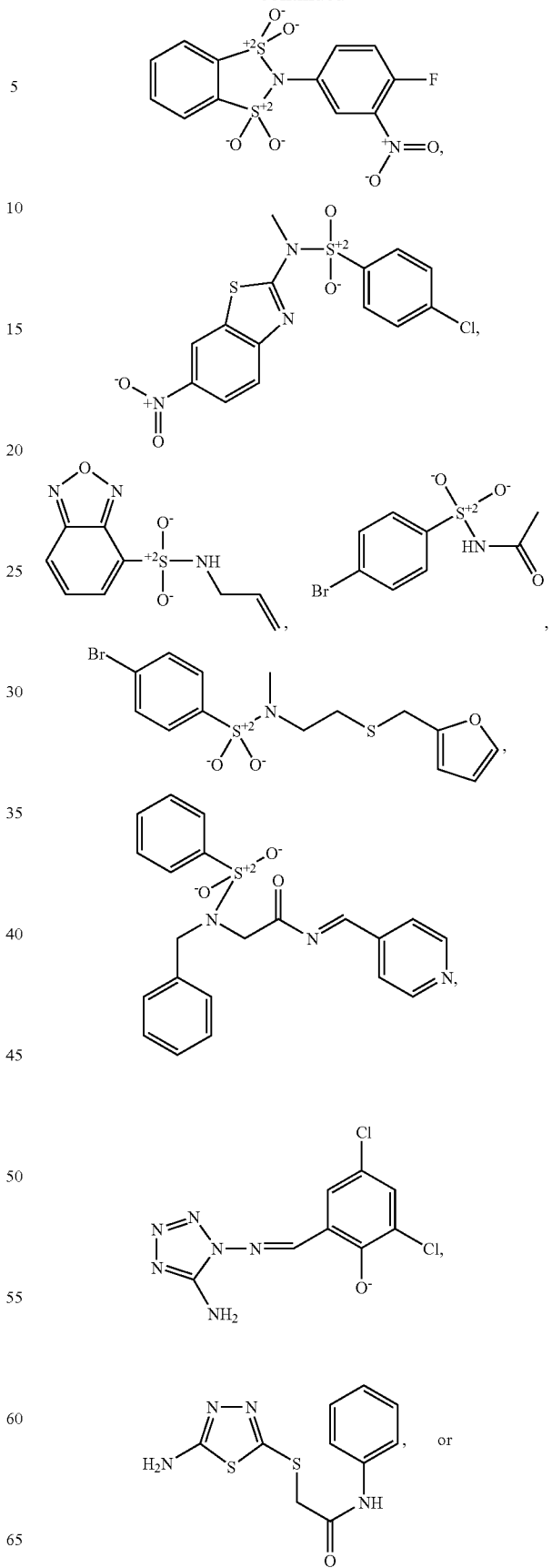

-continued

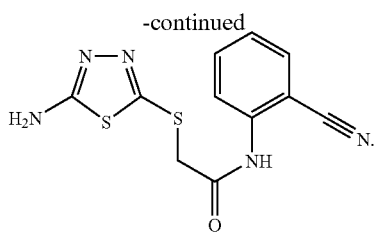

More preferably, the compound is one of the compounds set forth in FIG. 7, and most preferably is compound 57-6.

As used herein, "an amount of a compound effective to treat cancer in the mammal" means an amount of the compound that inhibits growth of a cancer or causes death of a cancer cell.

These methods can be used with any mammal. Preferably, the mammal is a human.

These methods are expected to be useful for treatment of any cancer, including prostate cancer; biliary tract cancer; brain cancer, including glioblastomas and medelloblastomas; breast cancer; cervical cancer; choriocarcinoma; colon cancer; endometrial cancer; esophageal cancer; gastric cancer; hematological neoplasms, including acute lymphocytic and myelogenous leukemia, multiple myeloma, AIDS associated leukemias and adult T-cell leukemia lymphoma; intraepithelial neoplasms, including Bowen's disease and Paget's disease; liver cancer; lung cancer; lymphomas, including Hodgkin's disease and lymphozytic lymphomas; neuroblastomas; oral cancer, including squamous cell carcinoma; ovarian cancer, including those arising from epithelial cells, stromal cells, germ cells and mesenchymal cells; pancreas cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma (teratomas, choriocarcinomas)), stromal tumors and germ cell tumors; thyroid cancer, including thyroid adenocarcinoma and medullar carcinoma; and renal cancer including adenocarcinoma and Wilms tumor. Preferably, the cancer is a lymphoma or a breast cancer. In accordance with the methods of treatment of the present invention, the compound is one of the compounds set forth in FIG. 7, and most preferably is compound 57-6.

Preferred embodiments of the invention are described in the following Example. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Small Molecule Inhibitors of BCL6

Example Summary

The ideal tool for targeting BCL6 would be a small molecule inhibitor. To that end, it was hypothesized that a region of the lateral groove interface rich in intermolecular contacts would be the optimal site to block corepressor binding. The side chains in this region are unique to BCL6 and required for binding corepressors, so that a small molecule inhibitor with high affinity to this site could be a potent and specific BCL6 inhibitor. Using computer-aided design on a million compound library, several compounds were identified that were subsequently shown to have the ability to disrupt BCL6 mediated repression in reporter assays and re-activate BCL6 target genes in BCR-type DLBCL cell lines, while displaying the same BCL6-dependent selectivity previously identified peptides in killing BCR type DLBCL but not 0x Phos DLBCL cells. Activity was in the high micromolar range. A structure/homology search yielded additional compounds with similar structures. These had equal or greater anti-BCL6 activity than the parent compound, confirming the inherent activity of these chemical structures.

Introduction

The role of structural biology in the drug design cycle is well established, and provides a critical link between chemists and biologists. The molecular details of how candidate drugs interact with their protein targets are absolutely required for computer-aided drug design (CADD), and this information is best obtained through high-resolution x-ray crystallography. This example describes the identification of small molecule BCL6 inhibitors. Initial lead compounds identified from highly efficient virtual in silico screens were evaluated in biological systems. Based on these results, improved candidates were postulated in silico. These second round candidates were then tested in biological systems.

The synergy between experimental structure determinations and virtual ligand screening is well established and forms an integral part of modern drug discovery (Muchmore and Hajduk, 2003; Noble et al., 2004; Williams et al., 2005). In some cases, visual inspection of crystal structures combined with good chemical intuition have lead to ideas for the favorable modifications of compounds. For example, a compound can be modified to include a favorable hydrogen bond to an adjacent protein side chain, or sections of a molecule that are not in contact with a binding site can be removed or minimized. Each particular case presents specific characteristics, and these are difficult to predict beforehand. The availability of a large number of compounds that bind to a similar region on a protein surface can be of tremendous benefit in deriving a "consensus structure", so that the best features of multiple chemical entities can be combined. High resolution 3D structural information is especially important for the structure-guided drug design process. Protein structures determined at lower resolution (say, 2.5 Å to 3.5 Å) are sufficient to trace the backbone and place most amino acid side chains with confidence, but are of limited value for identifying key drug-protein interactions. The structure at 2.2 Å has been determined for the human BCL6 BTB domain (see PCT Patent Publication WO 2005/058939 A2), which allows the visualization of the bound compounds with the required precision for computer-based methods (Macias et al., 2005; Huang et al., 2004). It is important that human proteins are used here, since even closely related homologs from other species may have subtle differences in binding surfaces, and these can have significant effects on drug binding.

Experimental

Figure 2:
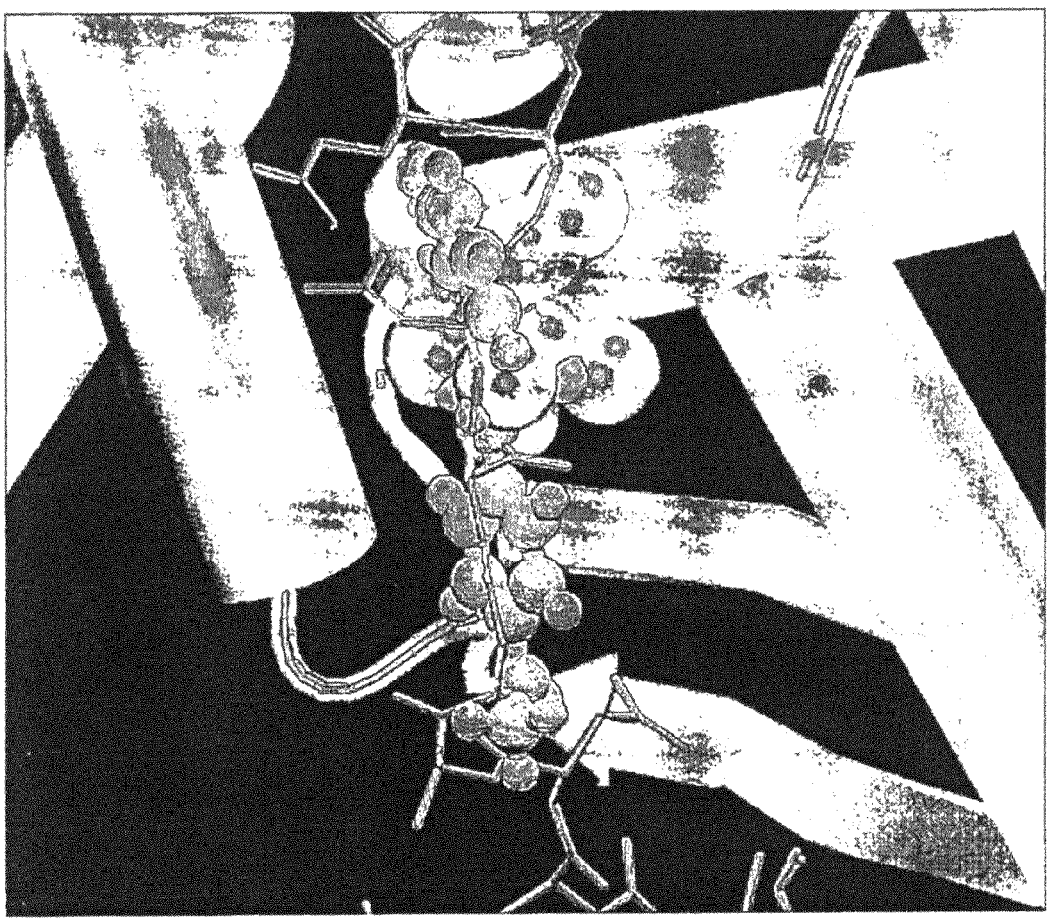
FIG. 2 is an image of one of the top 1K compounds (white) bound to one subunit of the BCL6 BTB dimer (cartoon) along with the SMRT BBD (stick) and the sphere set (dark balls) used to direct ligand placement.
Figure 3:
FIG. 3 is graphs of results of assays of three small molecule inhibitors of the BCL6 BTB lateral groove. The activity of the three inhibitors is shown in the 10-100 µM dose range. Panel A shows the results of the three inhibitors in the luciferase reporter assay—where the % loss of BTB repressor function vs. vehicle is shown above each bar. Panel B shows results of the QPCR assay of the BCL6 target genes CD69 and CCL3 after 8 hours exposure of Ly1 cells to drug #1 (dark) vs. vehicle (light). Panel C shows the % decrease in viability in Ly 1-BCR ("1"), Ly4 OxPhos ("4") and Ly7-BCR ("7") cells after 48 hours exposure to each of the three drugs vs. vehicle.

Database screening to identify compounds with the potential to bind to BCL6 and inhibit its biological activity was performed using the program DOCK (Ewing and Kuntz, 1997; Kuntz et al., 1982; Ewing et al., 2001). Starting from the crystal structure of the BCL6-SMRT peptide complex, the putative low molecular compound binding site was obtained by removing the SMRT peptide from the structure. The program SPHGEN was applied to identify appropriate bindings pockets in the region of BCL6 that binds the SMRT. A number of suitable sites were found, with the final site based on the SPHGEN spheres within 8 Å of residues 53 and 116 of chain B and 17 of chain A. This yielded 12 spheres defining the binding pocket. Visual inspection showed 2 of the spheres to be on the periphery of the putative binding region; these were deleted yielding a total of 10 spheres to be used to direct the docking process. A set of 1 million compounds was then screened against the binding pocket. A primary screen was performed with the top 50,000 compounds selected based on the normalized vdW attractive energy. The 50K compounds were then screened against 3 conformations of BCL6 (the crystal structure and 2 structures obtained from a 10 ns MD simulation of the apo protein). From the second screen, which includes additional optimization of the ligand during docking, the top 1000 compounds were selected based on the normalized total interaction energy using the most favorable energy against the 3 protein conformations for each ligand. The 1000 compounds were then subjected to chemical similarity clustering that involved two cycles of clustering with large clusters (>20 compounds) from the first cycle subjected to a second round of clustering. From the clusters, 199 compounds were selected based Lipinski's rule of 5, with emphasis on lower molecular weight compounds (~300 daltons) and reasonable solubilities (log P<5). FIG. 1 shows the molecular weight distributions of these compounds. An example of one of the compounds bound to BCL6 in silico is provided as FIG. 2. The 199 compounds were obtained from the appropriate vendor and were subjected to a luciferase reporter assay, described in PCT Patent Publication WO 2005/058939 A2. Compounds that showed the highest activity in the luciferase assay were also subjected to a QPCR assay and/or an assay to determine the effect of the compounds on the viability of BCR-type DLBCL cells, also as described in PCT Patent Publication WO 2005/058939 A2. Examples of results of these three assays are provided as FIG. 3. The tested compounds are shown in FIG. 4.

Figure 4A:
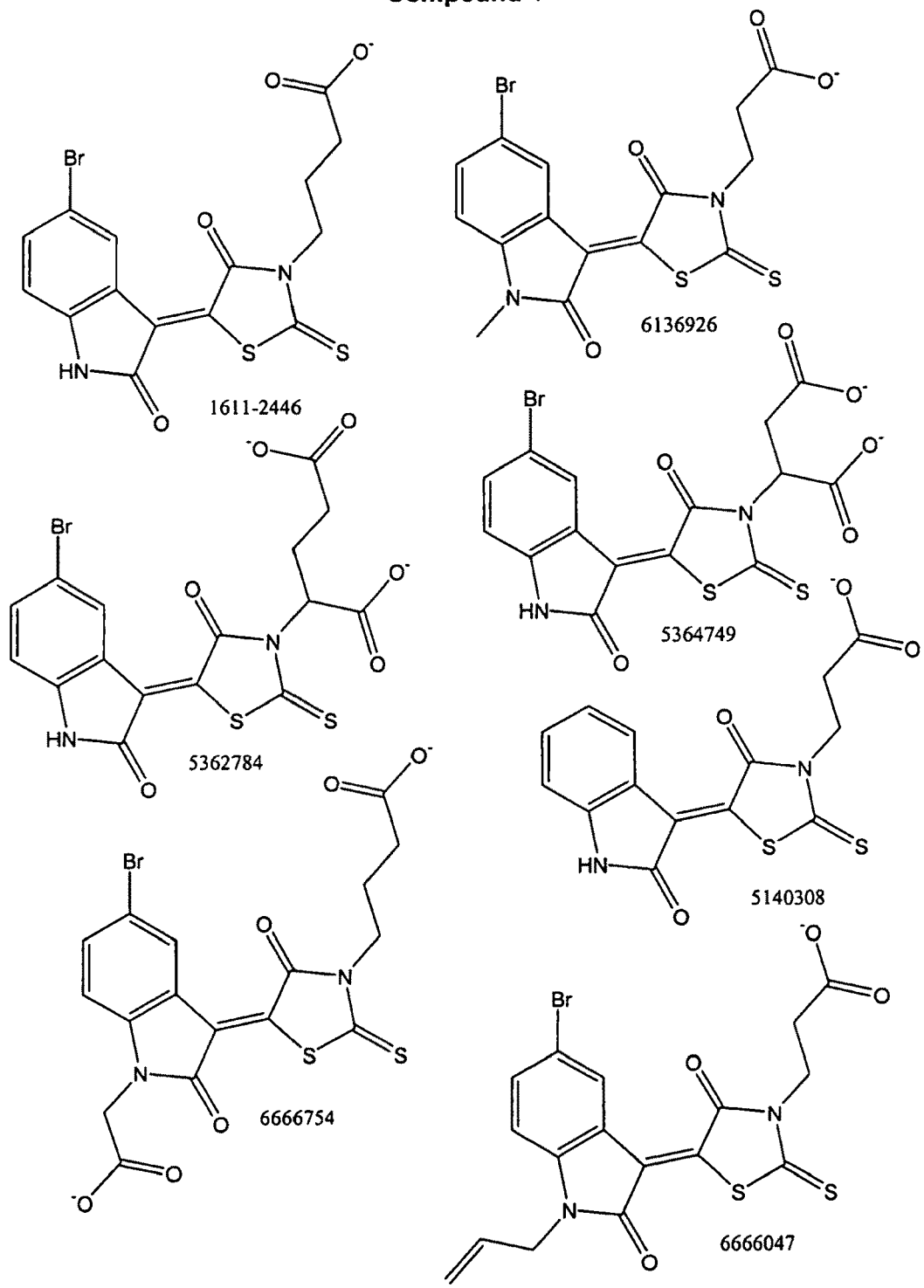
FIG. 4 shows the chemical structures of the compounds tested in the Example.
Figure 4B:
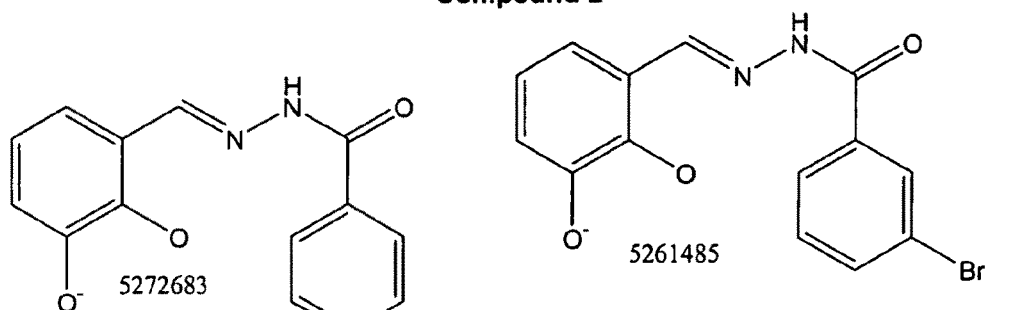
Figure 4B:
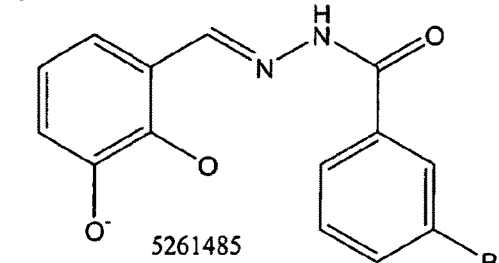
Figure 4B:
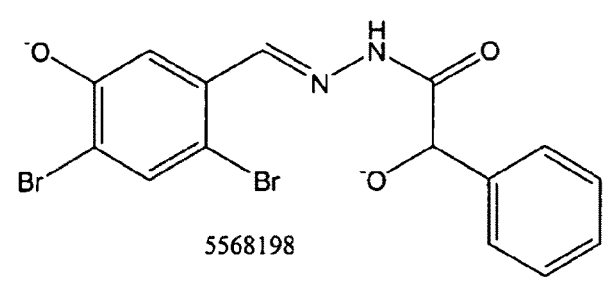
Figure 4B:
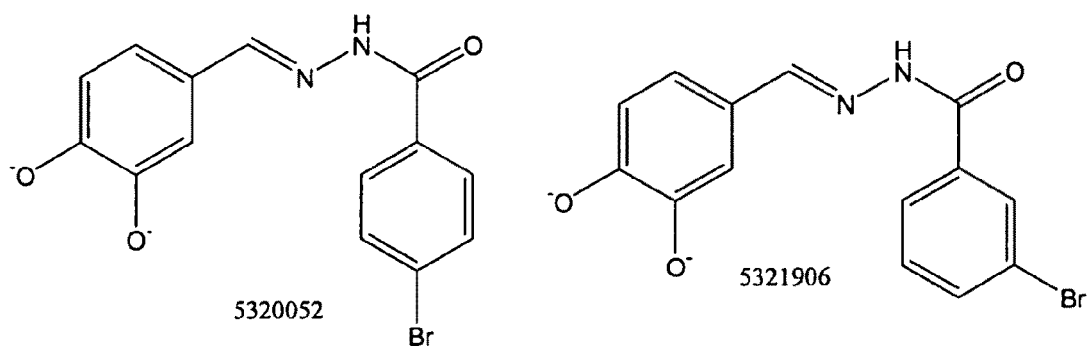
Figure 4B:
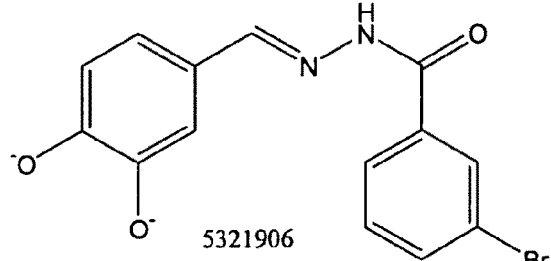
Figure 4C:
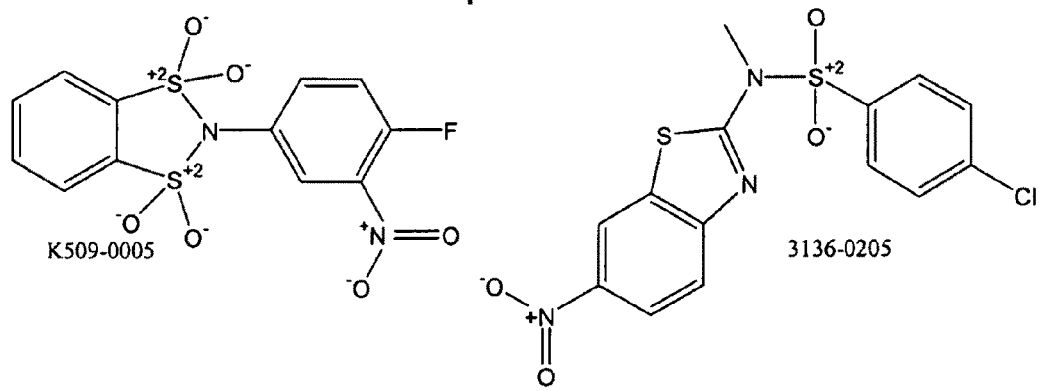
Figure 4C:
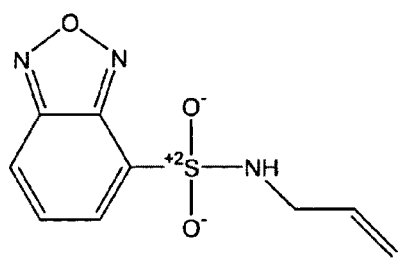
Figure 4C:
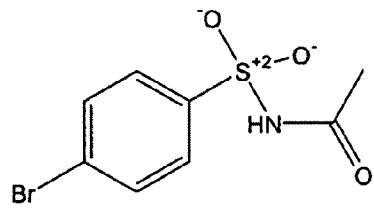
Figure 4C:
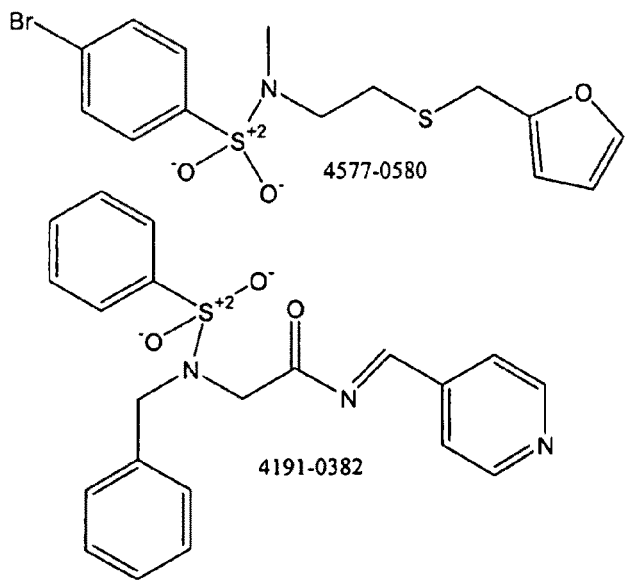
Figure 4D:
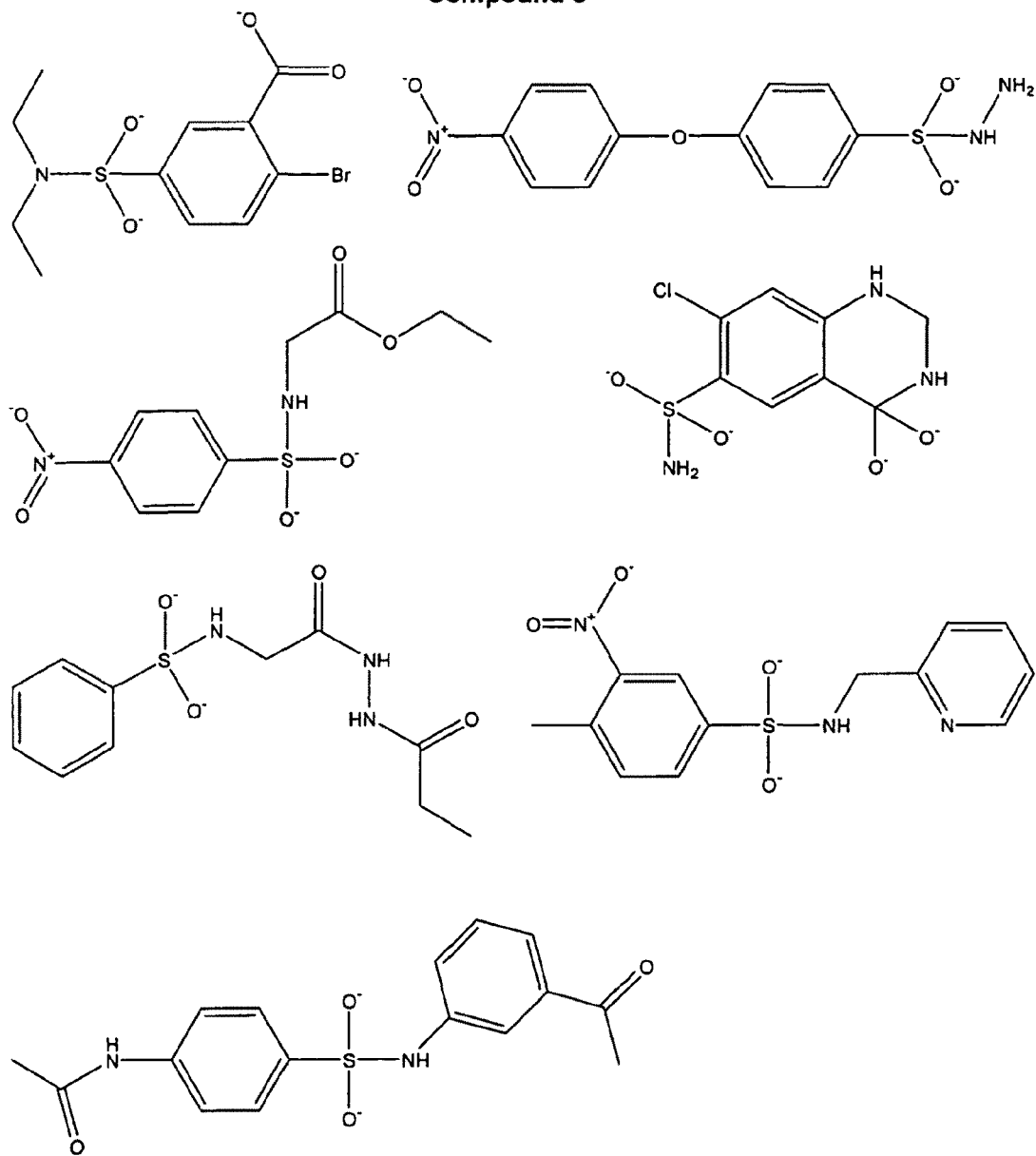
Figure 4E:
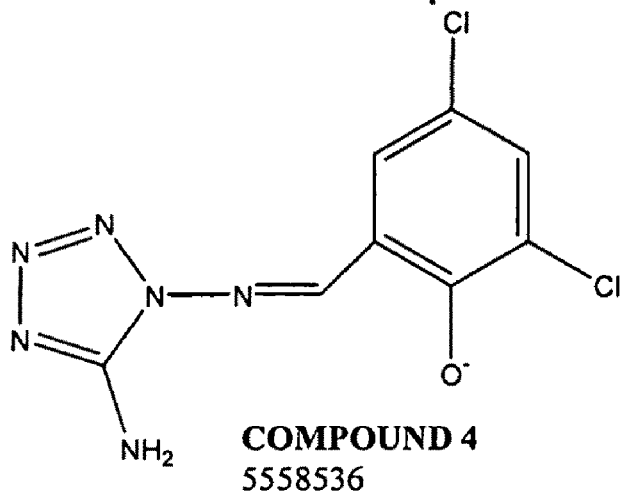
Figure 4E:
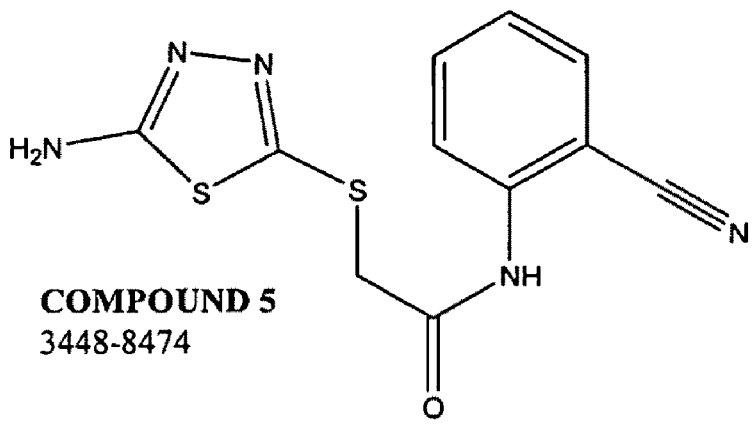
Figure 4E:
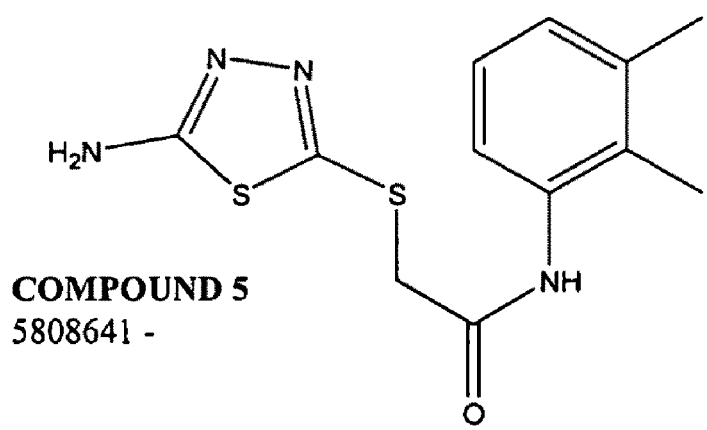
Figure 5:
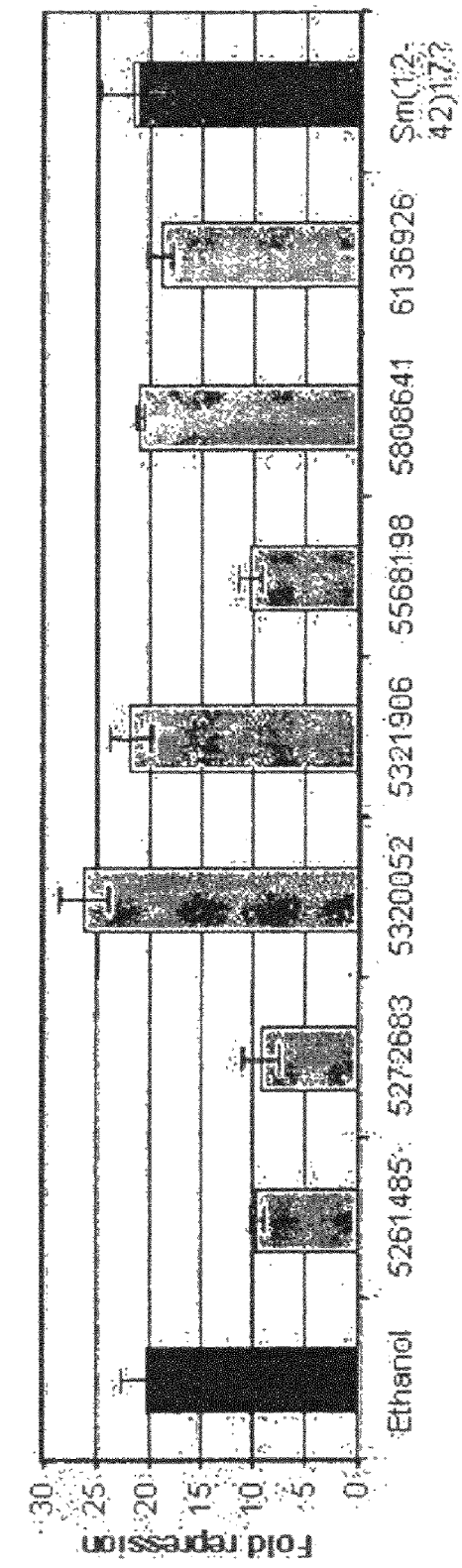
FIG. 5 is a graph showing the results of the luciferase assay on several compounds in FIG. 4.

From the initial 199 compounds that were assayed, 10 showed some level of biological activity. These were 1611-2446 (FIG. 4A); 5272683 (FIG. 4B); K509-0005, 3136-0205, 3660-0343, 0896-2057, 4577-0580, 4191-0382 (FIG. 4C); 5558536, and 3448-8474 (FIG. 4E). For each of these compounds structurally similar compounds were identified via fingerprint based similarity searching (see below). Approximately 30 new compounds were identified for each of the initial 10 (the remaining compounds from FIG. 4); these compounds were then obtained and subjected to the assays described above. About half of these compounds showed activity, validating the parent compounds as viable leads. FIG. 5 shows the results of a luciferase assay on several compounds in FIG. 4, including all the compounds of FIG. 4B.

Figure 6:
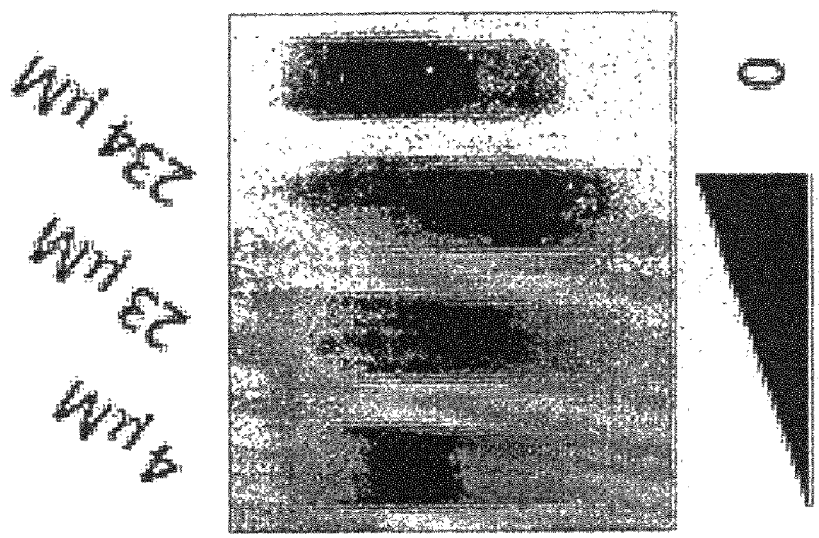
FIG. 6 is photographs of electrophoresed gels showing small molecule binding to BCL6 BIB domains. Candidate compounds were mixed with purified BCL6 BIB domain and run on native PAGE with Coomassie blue staining. A shift in the band position indicates complex formation. All lanes contained 175 µM BTB protein. A representative dosetitration experiment is shown with one of the compounds.
Figure 6:
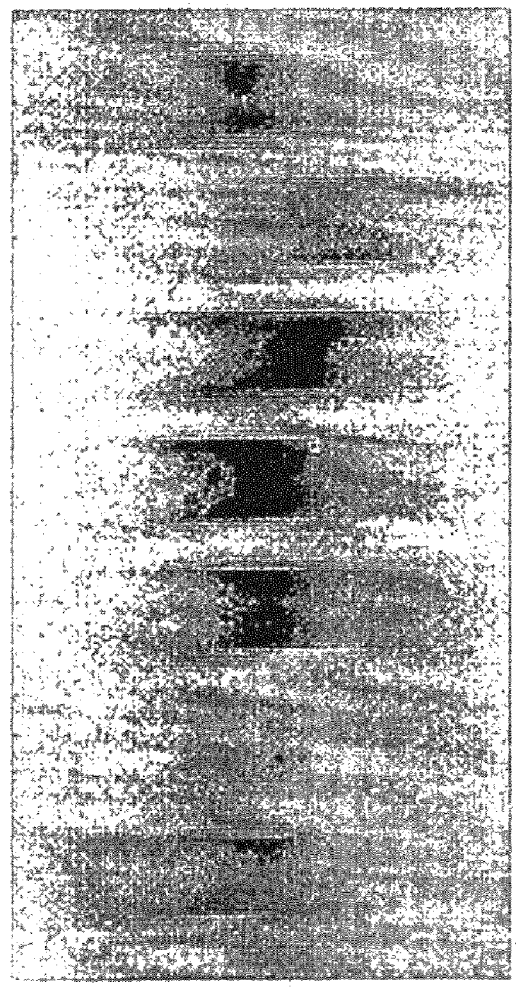

Several of the compounds were also tested with a binding assay, where purified BCL6 BTB domain was combined with a test compound, then run these on a non-denaturing PAGE (i.e. electrophoresis in the absence of SDS). A positive result is seen as a change in the mobility of the protein relative to a protein standard run without any compound. A weakness of this assay is that some compounds may bind but not produce a change in the mobility of the complex. Another possibility is that an inhibitor-protein complex may dissociate during the running of the gel, especially if the interaction is weak or has a high off-rate. Thus, a high rate of false negative results is expected. Despite these limitations, compounds that increased the mobility of BCL6 (reflecting an apparent increase in mass) were observed. See FIG. 6, showing an increase in mobility of BCL-6 in the presence of compound 1611-2446 and possibly 3136-0205 during electrophoresis.

EXAMPLE 2

Series 57 Compounds (FIG. 7)

Using these leads as molecular scaffolds we generated small libraries of molecules derived from each parental compound. The most active of these families was called the 57 series (see FIG. 7). Series 57 compounds could all specifically block BCL6 repression in reporter assays, and disrupt corepressor/BCL6 complexes at low micromolar concentrations as shown in fluorescence polarization assays. X-ray crystallography of the most active member of the 57 family (called 57-6) showed that the small molecule docked as predicted in the critical region of the lateral groove. Moreover, 57-6 induced an allosteric conformational change in the entire lateral groove that explains how these small molecules so effectively disrupt the BCL6/corepressor complex. 57-6 was also biologically active, since it could induce expression of BCL6 target genes including p53 and ATR in BCL6-positive diffuse large B-cell lymphoma (DLBCL) cells as shown by QPCR. 57-6 had no effect on negative control genes nor in BCL6-negative DLBCL cells. The mechanism of action was confirmed in ChIP assays showed that 57-6 abrogated BCL6 mediated corepressor recruitment to BCL6 target genes but had no effect on negative control genes. Most importantly, 57-6 specifically killed BCL6-positive DLBCL cells but had no effect on BCL6-negative DLBCL cells. A dose escalation experiment in mice revealed no toxic effects. In xenotransplantation experiments, 57-6 potently inhibited the growth of already established human DLBCL tumors in mice, again without toxicity to other organs.

REFERENCES

Abramson, J. S. and M. A. Shipp (2005). Advances in the biology and therapy of diffuse large B-cell lymphoma-moving towards a molecularly targeted approach. Blood, 106, 1164-74.

Adams, J., Kelso, R., and Cooley, L. (2000). The kelch repeat superfamily of proteins: propellers of cell function. Trends Cell Biol 10, 17-24.

Ahmad, K. F., Engel, C. K., and Privé, G. G. (1998). Crystal structure of the BTB domain from PLZF. Proc Natl Acad Sci USA 95, 12123-12128.

Ahmad, K. F., A. Melnick, S. Lax, D. Bouchard, J. Liu, C. L. Kiang, S. Mayer, S. Takahashi, J. D. Licht, and G. G. Prive (2003). Mechanism of SMRT corepressor recruitment by the BCL6 BTB domain. Mol Cell, 2003. 12(6): p. 1551-64.

Albagli-Curiel, O. (2003). Ambivalent role of BCL6 in cell survival and transformation. Oncogene 22, 507-516.

American Cancer Society (2005). Cancer Statistics. http://www.cancer.org/docroot/STT/stt_0.asp, 2005.

Ball, H. J., Melnick, A., Shaknovich, R., Kohanski, R. A., and Licht, J. D. (1999). The promyelocytic leukemia zinc finger (PLZF) protein binds DNA in a high molecular weight complex associated with cdc2 kinase. Nucleic Acids Res 27, 4106-4113.

Ball, L. J., Jarchau, T., Oschkinat, H., and Walter, U. (2002). EVH1 domains: structure, function and interactions. FEBS Lett 513, 45-52.

Bardwell, V. J., and Treisman, R. (1994). The POZ domain: a conserved protein-protein interaction motif. Genes Dev 8, 1664-1677.

Baron, B. W., Anastasi, J., Thirman, M. J., Furukawa, Y., Fears, S., Kim, D. C., Simone, F., Birkenbach, M., Montag, A., Sadhu, A., et al. (2002). The human programmed cell death-2 (PDCD2) gene is a target of BCL6 repression:

implications for a role of BCL6 in the down-regulation of apoptosis. Proc Natl Acad Sci USA 99, 2860-2865.

Basso, K., et al. (2005). Reverse engineering of regulatory networks in human B cells. Nat Genet 37, 382-90.

Blundell, T. L. & Patel, S. (2004). High-throughput X-ray crystallography for drug discovery. Curr Opin Pharmacol 4, 490-6.

Bos, R. et al. (2003). Oncogene 22, 8948.

Braisted, A. C. et al. (2003). J Am Chem Soc 125, 3714.

Brooks, B. et al. (1983). J Comput Chemistry 4, 187.

Brunger, A. T., Adams, P. D., Cloare, G. M., DeLano, W. L., Gros, P., Grosse-Kunstleve, R. W., Jiang, J. S., Kuszewski, J., Nilges, M., and Pannu, N. S. (1998). Crystallography & NMR system: a new software suite for macromolecular structure determination. Acta Crystallographica D54, 905-92.

Butina, D. (1999). J Chem Inf Comput Sci 39, 747.

Calame, K. L., Lin, K. I., and Tunyaplin, C. (2003). Regulatory mechanisms that determine the development and function of plasma cells. Annu Rev Immunol 21, 205-230.

Carlson, H. A. (2002). Curr Opin Chem Biol 6, 447.

Cattoretti, G. et al. (2005). Cancer Cell 7, 445.

Cattoretti, G., et al. (2005). Deregulated BCL6 expression recapitulates the pathogenesis of human diffuse large B cell lymphomas in mice. Cancer Cell 7, 445-55.

Chen, I. J., N. Neamati, A. D. MacKerell, Jr. (2002). Curr Drug Targets Infect Disord 2, 217.

Chen, W., Cooper, T. K., Zahnow, C. A., Overholtzer, M., Zhao, Z., Ladanyi, M., Karp, J. E., Gokgoz, N., Wunder, J. S., Andrulis, I. L., Levine, A. J., Mankowski, J. L. & Baylin, S. B. (2004). Epigenetic and genetic loss of Hid function accentuates the role of p53 in tumorigenesis. Cancer Cell 6, 387-98.

Cochran, A. G. (2000). Chem Biol 7, R85.

Cochran, A. G. (2001). Cum Opin Chem Biol 5, 654.

Connolly, M. L. (1983). Science 221, 709.

Costoya, J. A., and Pandolfi, P. P. (2001). The role of promyelocytic leukemia zinc finger and promyelocytic leukemia in leukemogenesis and development. Curr Opin Hematol 8, 212-217.

Cull, M. G., and Schatz, P. J. (2000). Biotinylation of proteins in vivo and in vitro using small peptide tags. Methods Enzymol 326, 430-440.

Daniel, J. M. and A. B. Reynolds. (1999). The catenin p120 (ctn) interacts with Kaiso, a novel BTB/POZ domain zinc finger transcription factor. Mol Cell Biol. 19, 3614-23.

David, G., Alland, L., Hong, S. H., Wong, C. W., DePinho, R. A., and Dejean, A. (1998). Histone deacetylase associated with mSin3A mediates repression by the acute promyelocytic leukemia-associated PLZF protein. Oncogene 16, 2549-2556.

DeGrazia, M. J., Thompson, J., Heuvel, J. P. & Peterson, B. R. (2003). Synthesis of a high-affinity fluorescent PPAR-gamma ligand for high-throughput fluorescence polarization assays. Bioorg Med Chem 11, 4325-32.

Deltour, S., Guerardel, C., and Leprince, D. (1999). Recruitment of SMRT/NCoR-mSin3A-HDAC-repressing complexes is not a general mechanism for BTB/POZ transcriptional repressors: the case of HIC-1 and gammaFBP-B. Proc Natl Acad Sci USA 96, 14831-14836.

Dent, A. L., Vasanwala, F. H., and Toney, L. M. (2002). Regulation of gene expression by the proto-oncogene BCL6. Crit. Rev Oncol Hematol 41, 1-9.

Dhordain, P., Albagli, O., Ansieau, S., Koken, M. H., Deweindt, C., Quief, S., Lantoine, D., Leutz, A., Kerckaert, J. P., and Leprince, D. (1995). The BTB/POZ domain targets the LAZ3/BCL6 oncoprotein to nuclear dots and mediates homomerisation in vivo. Oncogene 11, 2689-2697.

Dhordain, P., Albagli, O., Lin, R. J., Ansieau, S., Quief, S., Leutz, A., Kerckaert, J. P., Evans, R. M., and Leprince, D. (1997). Corepressor SMRT binds the BTB/POZ repressing domain of the LAZ3/BCL6 oncoprotein. Proc Natl Acad Sci USA 94, 10762-10767.

Dhordain, P., Lin, R. J., Quief, S., Lantoine, D., Kerckaert, J. P., Evans, R. M., and Albagli, O. (1998). The LAZ3(BCL6) oncoprotein recruits a SMRT/mSIN3A/histone deacetylase containing complex to mediate transcriptional repression. Nucleic Acids Res 26, 4645-4651.

Duncan, S. J. et al. (2001). J Am Chem Soc 123, 554.

Eads, C. A., A. E. Nickel, and P. W. Laird. (2002). Complete genetic suppression of polyp formation and reduction of CpG-island hypermethylation in Apc(Min/+) Dnmt1-hypomorphic Mice. Cancer Res. 62, 1296-9.

Enyedy, I. J. et al. (2001). J Med Chem 44, 4313.

Ewing, T., I. Kuntz. (1997). J Comput Chemistry 18, 1175.

Ewing, T. J. S. Makino, A. G. Skillman, I. D. Kuntz. (2001). J Comput Aided Mol Des 15, 411.

Fearon, D. T., Manders, P., and Wagner, S. D. (2001). Arrested differentiation, the self-renewing memory lymphocyte, and vaccination. Science 293, 248-250.

Ferrin, T. E., C. Huang, L. Jarvis, R. Langridge. (1988). J Mol Graphics 6.

Frankel, A. D. and Pabo, C. O. (1988). Cell 23, 1189-1193.

Garcia-Manero, G. and S. D. Gore. (2005). Future directions for the use of hypomethylating agents. Semin Hematol. 42, S50-9.

Godden, J. W., F. L. Stahura, J. Bajorath. (2005). J Chem Inf Model 45, 1812.

Gohlke, H., G. Klebe. (2002). Angew Chem Int Ed Engl 41, 2644.

Gohlke, H., G. Klebe. (2002). J Med Chem 45, 4153.

Goodford, P. J. (1984). J Med Chem 27, 558.

Grignani, F., De Matteis, S., Nervi, C., Tomassoni, L., Gelmetti, V., Cioce, M., Fanelli, M., Ruthardt, M., Ferrara, F. F., Zamir, I., et al. (1998). Fusion proteins of the retinoic acid receptor-alpha recruit histone deacetylase in promyelocytic leukaemia. Nature 391, 815-818.

Guidez, F., Ivins, S., Zhu, J., Soderstrom, M., Waxman, S., and Zelent, A. (1998). Reduced retinoic acid-sensitivities of nuclear receptor corepressor binding to PML- and PLZF-RARalpha underlie molecular pathogenesis and treatment of acute promyelocytic leukemia. Blood 91, 2634-2642.

Halgren, T. (1996). J Comput Chemistry 17, 520.

Halgren, T. (1999). J Comput Chemistry 20, 730.

Hamilton, A. C., Inglese, J., and Ferrer, M. (2003). A PDZ domain-based assay for measuring HIV protease activity: Assay design considerations. Protein Sci 12, 458-467.

Hancock, C. N. et al. (2005). J Med Chem 48, 4586.

Hancock, C. N., A. Macias, E. K. Lee, S. Yu, A. D. MacKerell, Jr. (2006). Medicinal Chemistry 2, 213.

He, L Z., Guidez, F., Triboli, C., Peruzzi, D., Ruthardt, M., Zelent, A., and Pandolfi, P. P. (1998). Distinct interactions of PML-RARalpha and PLZFRARalpha with co-repressors determine differential responses to RA in API Nat Genet. 18, 126-135.

Herold, S., Wanzel, M., Beuger, V., Frohme, C., Beul, D., Hillukkala, T., Syvaoja, J., Saluz, H. P., Haenel, F. & Eilers, M. (2002). Negative regulation of the mammalian UV response by Myc through association with Miz-1. Mol Cell 10, 509-21.

Hong, S. H., David, G., Wong, C. W., Dejean, A., and Privalsky, M. L. (1997). SMRT corepressor interacts with PLZF and with the PML-retinoic acid receptor alpha (RARalpha) and PLZF-RARalpha oncoproteins associated with acute promyelocytic leukemia. Proc Natl Acad Sci USA 94, 9028-9033.

Huang, N., Nagarsekar, A., Xia, G., Hayashi, J. & MacKerell, A. D., Jr. (2004). Identification of nonphosphate-containing small molecular weight inhibitors of the tyrosine kinase p56 Lck SH2 domain via in silico screening against the pY+3 binding site. J Med Chem 47, 3502-11.

Huynh, K. D., and Bardwell, V. J. (1998). The BCL6 POZ domain and other POZ domains interact with the co-repressors N-CoR and SM R1. Oncogene 17, 2473-2484.

Huynh, K. D., Fischle, W., Verdin, E., and Bardwell, V. J. (2000). BCoR, a novel corepressor involved in BCL6 repression. Genes Dev 14, 1810-1823.

Kaplan, J., and Calame, K. (1997). The ZiN/POZ domain of ZF5 is required for both transcriptional activation and repression. Nucleic Acids Res 25, 1108-1116.

Jain, A. N. (2004). Curr Opin Drug Discov Devel 7, 396.

Johnstone, R. W. and J. D. Licht. (2003). Histone deacetylase inhibitors in cancer therapy: is transcription the primary target? Cancer Cell 4, 13-8.

Kay, B. K., Williamson, M. P., and Sudol, M. (2000). The importance of being proline: the interaction of proline-rich motifs in signaling proteins with their cognate domains. FASEB J 14, 231-241.

Kenny, C. H., Ding, W., Kelleher, K., Benard, S., Dushin, E. G., Sutherland, A. G., Mosyak, L., Kriz, R. & Ellestad, G. (2003). Development of a fluorescence polarization assay to screen for inhibitors of the FtsZ/ZipA interaction. Anal Biochem 323, 224-33.

Kobayashi, A., Yamagiwa, H., Hoshino, H., Muto, A., Sato, K., Morita, M., Hayashi, N., Yamamoto, M., and Igarashi, K. (2000). A combinatorial code for gene expression generated by transcription factor Bach2 and MAZR (MAZ-related factor) through the BTB/POZ domain. Mol Cell Biol 20, 1733-1746.

Kondo, Y. and J. P. Issa. (2004). Epigenetic changes in colorectal cancer. Cancer Metastasis Rev: 23, 29-39.

Krek, W. (2003). BTB proteins as henchmen of Cul3-based ubiquitin ligases. Nat Cell Biol 5, 950-1.

Kreusch, A., Pfaffinger, P. J., Stevens, C. F., and Choe, S. (199.8). Crystal structure of the tetramerization domain of the Shaker potassium channel. Nature 392, 945-948.

Krumrine, J., F. Raubacher, N. Brooijmans, I. Kuntz. (2003). Methods Biochem Anal 44, 443.

Kuntz, I. D. (1992). Science 257, 1078.

Kuntz, I. D., J. M. Blaney, S. J. Oatley, R. Langridge, T. E. Ferrin. (1982). J Mol Biol 161, 269.

Kuppers, R., and Dalla-Favera, R. (2001). Mechanisms of chromosomal translocations in B cell lymphomas. Oncogene 20, 5580-5594.

Ladbury, J. E., Lemmon, M. A., Zhou, M., Green, J., Botfield, M. C., and Schlessinger, J. (1995). Measurement of the binding of tyrosyl phosphopeptides to SH2 domains: a reappraisal. Proc Natl Acad Sci USA 92, 3199-3203.

Lawrence, M. C., P. C. Davis. (1992). Proteins 12, 31.

Leach, A., I. Kuntz. (1992). J Comput Chemistry 13, 730.

Lee, M., M. Feig, F. Salsbury, C. Brooks. (2003). J Comput Chemistry 24, 1348.

Lemercier, C., Brocard, M. P., Puvion-Dutilleul, F., Kao, H. Y., Albagli, O., and Khochbin, S. (2002). Class II histone deacetylases are directly recruited by BCL6 transcriptional repressor. J Biol Chem 277, 22045-22052.

Li, J. Y., English, M. A., Ball, H. J., Yeyati, P. L., Waxman, S., and Licht, J. D. (1997). Sequence-specific DNA binding and transcriptional regulation by the promyelocytic leukemia zinc finger protein. J Biol Chem 272, 22447-22455.

Li, X., Peng, H., Schultz, D. C., Lopez-Guisa, J. M., Rauscher, F. J., 3rd, and Marmorstein, R. (1999). Structure-function studies of the BTB/POZ transcriptional repression domain from the promyelocytic leukemia zinc finger oncoprotein. Cancer Res 59, 5275-5282.

Li, Z., et al. (2003), A global transcriptional regulatory role for c-Myc in Burkitt's lymphoma cells. Proc Natl Acad Sci USA 100, 8164-9.

Lin, R. J., Nagy, L., Inoue, S., Shao, W., Miller, W. H., Jr., and Evans, R. M. (1998). Role of the histone deacetylase complex in acute promyelocytic leukaemia. Nature 391, 811-814.

Lin, R. J., Sternsdorf, T., Tini, M., and Evans, R. M. (2001). Transcriptional regulation in acute promyelocytic leukemia. Oncogene 20, 7204-7215.

Logarajah, S. et al. (2003) Oncogene 22, 5572.

Lokesh, G. L., Rachamallu, A., Kumar, G. D. & Natarajan, A. (2006). High-throughput fluorescence polarization assay to identify small molecule inhibitors of BRCT domains of breast cancer gene 1. Anal Biochem 352, 135-41.

Macias, A. T., Mia, M. Y., Xia, G., Hayashi, J. & MacKerell, A. D., Jr. (2005). Lead validation and SAR development via chemical similarity searching; application to compounds targeting the pY+3 site of the SH2 domain of p56lck. J Chem Inf. Model 45, 1759-66.

MacKerell, Jr., A. D., N. Banavali, N. Foloppe. (2000). Biopolymers 56, 257.

Maeda, T., Hobbs, R. M., Merghoub, T., Guernah, I., Zelent, A., Cordon-Cardo, C., Teruya-Feldstein, J. & Pandolfi, P. P. (2005). Role of the proto-oncogene Pokemon in cellular transformation and ARF repression. Nature 433, 278-85.

Mahmoudi, T., Katsani, K. R., and Verrijzer, C. P. (2002). GAGA can mediate enhancer function in trans by linking two separate DNA molecules. EMBO J. 21, 1775-1781.

Makino, S., I. Kuntz. (1997). J Comput Chemistry 18, 1812.

Markowitz, J. et al. (2004). J Med Chem 47, 5085.

Markowitz, J., A. D. Mackerell, Jr., F. Carrier, T. H. Charpentier, D. J. Weber. (2005). Curr Top Med Chem 5, 1093.

Martin, Y. C. (1992). J Med Chem 35, 2145.

McConnell, M. J., Chevallier, N., Berkofsky-Fessler, W., Giltnane, J. M., Malani, R. B., Staudt, L. M. & Licht, J. D. (2003). Growth suppression by acute promyelocytic leukemia-associated protein PLZF is mediated by repression of c-myc expression. Mol Cell Biol 23, 9375-88.

McGregor, C. L., Chen, L., Pomroy, N. C., Hwang, P., Go, S., Chakrabartty, A. & Prive, G. G. (2003). Lipopeptide detergents designed for the structural study of membrane proteins. Nat Biotechnol 21, 171-6.

McQuarrie, D. (1976) Statistical Mechanics, Harper & Row, New York

Melnick, A. (2005). Predicting the Effect of Transcription Therapy in Hematologic Malignancies. Leukemia 19, 1109-17.

Melnick, A., and Licht, J. D. (1999). Deconstructing a disease: RARalpha, its fusion partners, and their roles in the pathogenesis of acute promyelocytic leukemia. Blood 93, 3167-3215.

Melnick, A. and J. D. Licht. (2002). Histone deacetylases as therapeutic targets in hematologic malignancies. Curr Opin Hematol, 9, 322-32.

Melnick, A., Ahmad, K. F., Arai, S., Polinger, A., Ball, H., Borden, K. L., Carlile, G. W., Privé, G. G., and Licht, J. D. (2000). In-depth mutational analysis of the promyelocytic leukemia zinc finger BTB/POZ domain reveals motifs and residues required for biological and transcriptional functions. Mol Cell Biol 20, 6550-6567.

Melnick, A., Carlile, G., Ahmad, K. F., Kiang, C. L., Corcoran, C., Bardwell, V., Prive, G. G., and Licht, J. D. (2002). Critical residues within the BTB domain of PLZF and BCL6 modulate interaction with corepressors. Mol Cell Biol 22; 1804-1818.

Melnick, A. M., K. Adelson, and J. D. Licht. (2005). The theoretical basis of transcriptional therapy of cancer: can it be put into practice? J Clin Oncol, 23, 3957-70.

Meng, E. C., I. D. Kuntz, D. J. Abraham, G. E. Kellogg. (1994). J Comput Aided Mol Des 8, 299.

Muchmore, S. W. & Hajduk, P. J. (2003). Crystallography, NMR and virtual screening: integrated tools for drug discovery. Curr Opin Drug Discov Devel 6, 544-9.

Ng D, Thakker N, Corcoran C M, Donnai D, Perveen R, Schneider A, Hadley D W, Tifft C, Zhang L, Wilkie A O, van der Smagt J J, Gorlin R J, Burgess S M, Bardwell V J, Black G C, Biesecker L G. (2004). Nat. Genet. 36, 411-416.

Nikolovska-Coleska, Z., Wang, R., Fang, X., Pan, H., Tomita, Y., Li, P., Roller, P. P., Krajewski, K., Saito, N. G., Stuckey, J. A. & Wang, S. (2004). Development and optimization of a binding assay for the XIAP BIR3 domain using fluorescence polarization. Anal Biochem 332, 261-73.

Niu, H. (2002). The proto-oncogene BCL6 in normal and malignant B cell development. Hematol Oncol 20, 155-166.

Niu, H., Cattoretti, G., and Dalla-Favera, R. (2003). BCL6 Controls the Expression of the B7-1/CD80 Costimulatory Receptor in Germinal Center B Cells. J Exp Med 198, 211-221.

Noble, M. E., Endicott, J. A. & Johnson, L. N. (2004). Protein kinase inhibitors: insights into drug design from structure. Science 303, 1800-5.

Ogino, S., et al. (2006). CpG island methylator phenotype (CIMP) of colorectal cancer is best characterized by quantitative DNA methylation analysis and prospective cohort studies. Gut 55, 1000-6.

Oprea, T., C. Ho, G. Marshall. (1995). paper presented at the American Chem. Soc. Meeting, Washington D. C.

Otwinowski, Z., and Minor, W. (1997). Processing of X-ray diffraction data collected in oscillation mode. Methods in Enzymology: Macromolecular Crystallography Part A 276, 307-326.

Owicki, J. C. (2000). Fluorescence polarization and anisotropy in high throughput screening: perspectives and primer. J Biomol Screen 5, 297-306.

Pan, Y., N. Huang, S. Cho, A. D. MacKerell, Jr. (2003). J Chem Inf Comput Sci 43, 267.

Pandolfi, P. P. (2001). Transcription therapy for cancer. Oncogene 20, 3116-27.

Pasqualucci, L., Migliazza, A., Basso, K., Houldsworth, J., Chaganti, R. S., and Dalla-Favera, R. (2003). Mutations of the BCL6 proto-oncogene disrupt its negative autoregulation in diffuse large B-cell lymphoma. Blood 101, 2914-2923.

Pawson, T., and Nash, P. (2003). Assembly of cell regulatory systems through protein interaction domains. Science 300, 445-452.

Peukert, K., Staller, P., Schneider, A., Carmichael, G., Hanel, F. & Eilers, M. (1997). An alternative pathway for gene regulation by Myc. Embo J 16, 5672-86.

Phan, R. T., Saito, M., Basso, K., Niu, H. & Dalla-Favera, R. (2005). BCL6 interacts with the transcription factor Miz-1 to suppress the cyclin-dependent kinase inhibitor p21 and cell cycle arrest in germinal center B cells. Nat Immunol 6, 1054-60.

Pintard, L., Willems, A. & Peter, M. (2004). Cullin-based ubiquitin ligases: Cul3-BTB complexes join the family. Embo J 23, 1681-7.

Pinte, S., Stankovic-Valentin, N., Deltour, S., Rood, B. R., Guerardel, C. & Leprince, D. (2004). The tumor suppressor gene HIC1 (hypermethylated in cancer 1) is a sequence-specific transcriptional repressor: Definition of its consensus binding sequence and analysis of its DNA binding and repressive properties. J Biol Chem 383, 13-24.

Polo, J. M., T. Dell'Oso, S. M. Ranuncolo, L. Cerchietti, D. Beck, G. F. Da Silva, G. G. Prive, J. D. Licht, and A. Melnick (2004). Specific peptide interference reveals BCL6 transcriptional and oncogenic mechanisms in B-cell lymphoma cells. Nat Med 10, 1329-35.

Prehoda, K. E., Lee, D. J., and Lim, W. A. (1999). Structure of the enabled/VASP homology 1 domain-peptide complex: a key component in the spatial control of actin assembly. Cell 97, 471-480.

Prive, G. G., A. Melnick. (2006). Curr Opin Genet Dev 16, 71.

Prokhortchouk, E. and B. Hendrich. (2002). Methyl-CpG binding proteins and cancer: are MeCpGs more important than MBDs? Oncogene 21, 5394-9.

Prokhortchouk, A., et al. (2001). The p120 catenin partner Kaiso is a DNA methylation-dependent transcriptional repressor. Genes Dev. 15, 1613-8.

Prokhortchouk A. et al. (2006). Mol Cell Biol 26, 199.

Qiu, D., P. Shenkin, F. Hollinger, C. Still. (1997). J Phys Chem 101, 3005.

Ranuncolo, S. M. and A. Melnick (2005). Unpublished data.

Ryckaert, J., G. Ciccotti, H. Berendson. (1977). J. Comput. Physics 23, 327.

Samowitz, W. S., et al. (2005). Evaluation of a large, population-based sample supports a CpG island methylator phenotype in colon cancer. Gastroenterology 129, 837-45.

Scheldrick, G. M., and Schneider, T. R. (1997). SHELXL: high-resolution refinement. Methods Enzymol 277, 319-343.

Schneider, G., M. L. Lee, M. Stahl, P. Schneider. (2000). J Comput Aided Mol Des 14, 487.

Shaffer, A. L., Lin, K. I., Kuo, T. C., Yu, X., Hurt, E. M., Rosenwald, A., Giltnane, J. M., Yang, L., Zhao, H., Calanie, K., and Staudt, L. M. (2002). Blimp-1 orchestrates plasma cell differentiation by extinguishing the mature B cell gene expression program. Immunity. 17, 51-62.

Shaffer, A. L., Yu, X., He, Y., Boldrick, J., Chan, E. P., and Staudt, L. M. (2000). BCL6 represses genes that function in lymphocyte differentiation, inflammation, and cell cycle control. Immunity 13, 199-212.

Shen, H. M., Peters, A., Baron, B., Zhu, X., and Storb, U. (1998). Mutation of BCL6 gene in normal B cells by the process of somatic hypermutation of 1 g genes. Science 280, 1750-1752.

Shipp, M. A., et al. (2002). Diffuse large B-cell lymphoma outcome prediction by gene-expression profiling and supervised machine learning. Nat. Med. 8, 68-74.

Silverman, L. R., et al. (2002). Randomized controlled trial of azacitidine in patients with the myelodysplastic syndrome: a study of the cancer and leukemia group B. J Clin Oncol. 20, 2429-40.

Staudt, L. M. (2002). Gene expression profiling of lymphoid malignancies. Annu Rev Med 53, 303-318.

Stebbins, C. E., Kaelin, W. G., Jr., and Pavletich, N. P. (1999). Structure of the VHL-ElonginC-ElonginB complex: implications for VHL tumor suppressor function. Science 284, 455-461.

Stogios, P. J., Downs, G. S., Jauhal, J. J., Nandra, S. K. & Prive, G. G. (2005) Sequence and structural analysis of BTB domain proteins. Genome Biol 6, R82.

Sudol, M., Sliwa, K., and Russo, T. (2001). Functions of WW domains in the nucleus. FEBS Lett 490, 190-195.

Swaan, P., in Burger's Medicinal Chemistry and Drug Discovery. (2003).

Taylor, R. D., P. J. Jewsbury, J. W. Essex. (2002) J Comput Aided Mol Des 16, 151.

Teague, S. J., A. M. Davis, P. D. Leeson, T. Oprea. (1999). Angew Chem Int Ed Engl 38, 3743.

Terwilliger, T. C., and Berendzen, J. (1999). Automated MAD and MIR structure solution. Acta Crystallogr D Biol Crystallogr 55 (Pt 4), 849-861.

Toney, L. M., Cattoretti, G., Graf, J. A., Merghoub, T., Pandolfi, P. P., Dalla-Favera, R., Ye, B. H., and Dent, A. L. (2000). BCL6 regulates chemokine gene transcription in macrophages. Nat Immunol 1, 214-220.

Toyota, M., et al. (1999). CpG island methylator phenotype in colorectal cancer. Proc Natl Acad Sci USA. 96, 8681-6.

Velazquez Campoy, A. & Freire, E. (2005). ITC in the post-genomic era . . . ? Priceless. Biophys Chem 115, 115-24.

Veselovsky, A. V. A. S. Ivanov. (2003). Curr Drug Targets Infect Disord 3, 33.

Wallace A C, Laskowski R A & Thornton J M (1995). LIGPLOT: A program to generate schematic diagrams of protein-ligand interactions. Prot. Eng., 8, 127-0.134.

Wang, X., Li, Z., Naganuma, A., and Ye, B. H. (2002). Negative autoregulation of BCL6 is bypassed by genetic alterations in diffuse large B cell lymphomas. Proc Natl Acad Sci USA 99, 15018-15023.

Williams, S. P., Kuyper, L. F. & Pearce, K. H. (2005). Recent applications of protein crystallography and structure-guided drug design. Curr Opin Chem Biol 9, 371-80.

Wong, C. W., and Privalsky, M. L. (1998). Components of the SMRT corepressor complex exhibit distinctive interactions with the POZ domain oncoproteins PLZF, PLZF-RARalpha, and BCL6. J Biol Chem 273, 27695-27702.

Wong, S., et al. (2004). Sole BCR-ABL inhibition is insufficient to eliminate all myeloproliferative disorder cell populations. Proc Natl Acad Sci USA. 101, 17456-61.

Ye, B. H. (2000). BCL6 in the pathogenesis of non-Hodgkin's lymphoma. Cancer Invest 18, 356-365.

Ye, B. H. (2001). The Role of Bcl-6 in Normal Lymphoid System and Non-Hodgkin's Lymphomas, in Transcription Factors: Normal and Malignant Development of Blood Cells, K. Ravid and J. D. Licht, Editors. John Wiley & Sons: New York. p. 271-289.

Xu, L., Wei, Y., Reboul, J., Vaglio, P., Shin, T. H., Vidal, M., Elledge, S. J. & Harper, J. W. (2003). BTB proteins are substrate-specific adaptors in an SCF-like modular ubiquitin ligase containing CUL-3. Nature 425, 316-21.

Yoon, H. G., D. W. Chan, A. B. Reynolds, J. Qin, J. Wong. (2003). Mol Cell 12, 723.

Zelent, A., Guidez, F., Melnick, A., Waxman, S., and Licht, J. D. (2001). Translocations of the RARalpha gene in acute promyelocytic leukemia. Oncogene 20, 7186-7203.

Zhang, J. H., Chung, T. D. & Oldenburg, K. R. (1999). A Simple Statistical Parameter for Use in Evaluation and Validation of High Throughput Screening Assays. J Biomol Screen 4, 67-73.

Zhang, H., Okada, S., Hatano, M., Okabe, S., and Tokuhisa, T. (2001). A new functional domain of Bcl6 family that recruits histone deacetylases. Biochim Biophys Acta 1540, 188-200.

Ziegelbauer, J., Shan, B., Yager, D., Larabell, C., Hoffmann, B. & Tjian, R. (2001). Transcription factor MIZ-1 is regulated via microtubule association. Mol Cell 8, 339-49.

Zollman, S., Godt, D., Prive, G. G., Couderc, J. L.& Laski, F. A. (1994). The BTB domain, found primarily in zinc finger proteins, defines an evolutionarily conserved family that includes several developmentally regulated genes in Drosophila. Proc Natl Acad Sci U S A 91, 10717-21.

PCT Patent Publication WO 2005/058939 A2.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound having the structure:

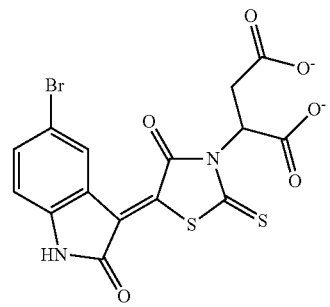

or a pharmaceutically acceptable salt thereof.

2. A composition for inhibiting BCL6 comprising the compound of claim 1.

3. A pharmaceutical composition comprising the compound of claim 1 and a pharmaceutically acceptable carrier.

4. The pharmaceutical composition of claim 3, formulated for parenteral administration.

5. A compound having the structure:

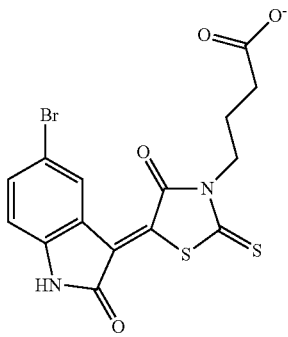

or a pharmaceutically acceptable salt thereof.

6. A composition for inhibiting BCL6 comprising the compound of claim 5.

7. A pharmaceutical composition comprising the compound of claim 5 and a pharmaceutically acceptable carrier.

8. The pharmaceutical composition of claim 7, formulated for parenteral administration.

9. A compound having the structure:

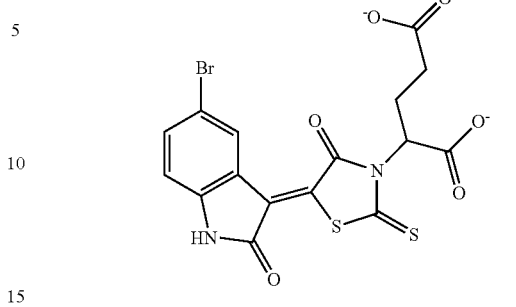

or a pharmaceutically acceptable salt thereof.

10. A composition for inhibiting BCL6 comprising the compound of claim 9.

11. A pharmaceutical composition comprising the compound of claim 9 and a pharmaceutically acceptable carrier.

12. The pharmaceutical composition of claim 11, formulated for parenteral administration.

\* \* \* \* \*